United States Patent [19]

Ernest et al.

[11] Patent Number: 4,614,614
[45] Date of Patent: Sep. 30, 1986

[54] PROCESS FOR THE MANUFACTURE OF OPTICALLY ACTIVE AZETIDINONES

[75] Inventors: Ivan Ernest, Birsfelden; Jaroslav Kalvoda, Binningen; Wolfgang Fröstl, Basel, all of Switzerland

[73] Assignee: Ciba-Geigy Corporation, Ardsley, N.Y.

[21] Appl. No.: 592,312

[22] Filed: Mar. 22, 1984

[30] Foreign Application Priority Data

Mar. 28, 1983 [CH] Switzerland .................. 1678/83

[51] Int. Cl.$^4$ ................... C07D 205/08; C07D 303/48
[52] U.S. Cl. ................... 540/359; 549/548; 560/9; 560/39; 560/43; 540/200
[58] Field of Search ................... 260/239 A

[56] References Cited

U.S. PATENT DOCUMENTS 4,432,901  2/1984  Lempert .................. 260/239 AL
4,436,661  3/1984  Pfaendler .................. 260/239 A

OTHER PUBLICATIONS

Yanagisawa et al., Tet. Letters 24, 1037 (1983).
Longo et al., Tet. Letters 22, 355 (1981).
Neider et al., Tet. Letters 23, 2293-96 (1982).
"Organic Chemistry", 4th Edition, Morrison & Boyd, pp. 204-205.
Derwent Abstract 98297 E146 fa Japan 57/163,362 (1981).
Shiozaki et al., Tet. Letters 22, 5205 (1981).

*Primary Examiner*—Mark L. Berch
*Attorney, Agent, or Firm*—Karl F. Jorda; Michael W. Glynn; Bruce M. Collins

[57] ABSTRACT

The present invention relates to an improved process for the manufacture of (3S)-3,4-trans-disubstituted azetidinones of the formula

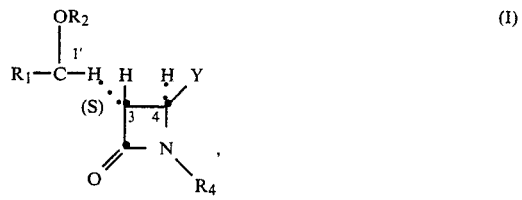

in which $R_1$ represents hydrogen or lower alkyl,
$R_2$ represents hydrogen or a hydroxy-protecting group,
Y represents the group —S(=O)—$R_3$ or —S(=O)$_2$—$R_3$ wherein $R_3$ represents an organic radical bonded to the sulphur atom by a carbon atom that is not bonded to hydrogen, or the group —C(=O)—O—$R_3'$ wherein $R_3'$ represents an organic radical bonded to the oxygen atom of the carboxy group by a carbon atom that is not bonded to hydrogen, or a carboxy-protecting group, and
$R_4$ represents hydrogen or an amino-protecting group $R_4'$.

The process according to the invention is carried out under particularly forvorable reacton conditions and yields compounds (I) in particularly high yields.

19 Claims, No Drawings

PROCESS FOR THE MANUFACTURE OF OPTICALLY ACTIVE AZETIDINONES

The present invention relates to an improved process for the manufacture of (3S)-3,4-trans-disubstituted azetidinones of the formula

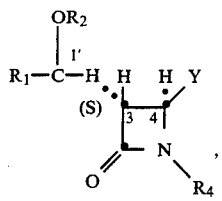

in which
R$_1$ represents hydrogen or lower alkyl,
R$_2$ represents hydrogen or a hydroxy-protecting group,
Y represents the group —S(=O)—R$_3$ or —S(=O)$_2$—R$_3$ wherein R$_3$ represents an organic radical bonded to the sulphur atom by a carbon atom that is not bonded to hydrogen, or the group —C(=O)—O—R$_3'$ wherein R$_3'$ represents an organic radical bonded to the oxygen atom of the carboxy group by a carbon atom that is not bonded to hydrogen, or a carboxy-protecting group, and
R$_4$ represents hydrogen or an amino-protecting group R$_4'$,
and in which the 4-carbon atom of the azetidinone ring has the R-configuration if Y represents the group —S(=O)—R$_3$ or —S(=O)$_2$—R$_3$, and the S-configuration if Y represents the group —C(=O)—O—R$_3'$, and the 1'-carbon atom of the side chain has the R- or S-configuration if R$_1$ represents lower alkyl.

Compounds of the formula I in which R$_1$ represents methyl, R$_2$ represents hydrogen or methoxymethyl, Y represents benzenesulphonyl and R$_4$ represents hydrogen, 4-methoxyphenyl or 3,4-dimethoxyphenyl, and their manufacture by cyclisation with n-butyllithium at −50° C. are known from Yanagisawa H. et al., Tetrahedron Letters 24 [10], 1037–1040 (1983).

Compounds of the formula I in which R$_1$ represents methyl, R$_2$ represents hydrogen or dimethyl-tert.-butylsilyl, Y represents tert.-butoxycarbonyl and R$_4$ represents 2,4-dimethoxybenzyl, and their manufacture by cyclisation with lithium bistrimethylsilylacetamide are known from Shiozaki M. et al., Tetrahedron Letters 22 [51], 5205–5208 (1981).

The process according to the invention has the advantage that under particularly favourable reaction conditions compounds of the formula I are obtained in relatively high yields.

The process according to the invention is characterised in that a compound of the formula

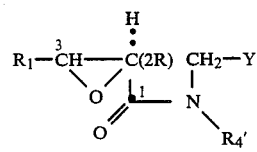

in which Y and R$_1$ have the meanings given under formula I and R$_4'$ represents a suitable aminoprotecting group, and the 2-carbon atom has the R-configuration and, if R$_1$ represents lower alkyl, the 3-carbon atom has the R- or the S-configuration, or a compound of the formula

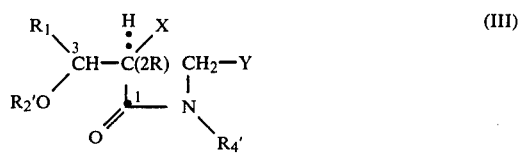

in which Y and R$_1$ have the meanings given under formula I, R$_2'$ represents a hydroxy-protecting group that cannot be removed under the conditions of the cyclisation operation, R$_4'$ represents a suitable amino-protecting group and X represents a nucleofugal group, and the 2-carbon atom has the R-configuration and, if R$_1$ represents lower alkyl, the 3-carbon atom has the R- or the S-configuration, is reacted with a reagent that yields fluoride ions in an aprotic organic solvent, and, if desired, a resulting compound of the formula I is converted into a different compound of the formula I in accordance with the definition.

In the description of the present invention, the term "lower" used in connection with groups or radicals, for example lower alkyl, lower alkoxy, lower alkanoyl etc., means that, unless expressly defined otherwise, the groups or radicals so designated contain up to and including 7, preferably up to and including 4, carbon atoms.

The general definitions used hereinbefore and hereinafter preferably have the following meanings within the framework of the present description:

Lower alkyl R$_1$ is preferably methyl, also ethyl, n-propyl, isopropyl, n-butyl, isobutyl or tert.-butyl.

R$_1$ is preferably hydrogen or methyl.

Hydroxy-protecting groups R$_2$ and their introduction and removal are described, for example, in "Protective Groups in Organic Chemistry", Plenum Press, London and New York 1973, and in "Protective Groups in Organic Chemistry", Wiley, N.Y. 1974.

A hydroxy-protecting group R$_2$ is, for example, the acyl group of a substituted carboxylic or sulphonic acid, for example lower alkanoyl substituted by halogen, for example fluorine or chlorine, for example 2,2-dichloro- or 2,2,2-trifluoro-acetyl, the acyl group of a carbonic acid semiester substituted, for example, by halogen, for example chlorine, phenyl or by p-nitrophenyl, for example 2,2,2-trichloroethoxycarbonyl, allyloxycarbonyl, benzyloxycarbonyl or p-nitrobenzyloxycarbonyl, 2-oxa- or 2-thia-cycloalkyl having from 5 to 7 ring atoms, for example 2-tetrahydrofuryl or 2-tetrahydropyranyl or a thia analogue thereof, or 1-lower alkoxy-lower alkyl, for example methoxymethyl or 1-ethoxyethyl.

A suitable hydroxy-protecting group R$_2$ is preferably the substituted acyl group of a carbonic acid semiester, for example 2,2,2-trichloroethoxycarbonyl, allyloxycarbonyl, benzyloxycarbonyl or p-nitrobenzyloxycarbonyl, or a silyl group, for example tri-lower alkylsilyl, for example trimethyl- or triethyl-silyl, di-lower alkyl-trisubstituted methylsilyl, for example dimethyl- or diethyl-2-ethyl-2-propylsilyl or dimethyl-tert.-butylsilyl, di-aryl-lower alkylsilyl, for example diphenyl-tert.-butylsilyl, aryl-lower alkylsilyl, for example tert.-butyl-methyl-phenylsilyl, and tri-(lower alkyl)-aryloxy-di-lower alkylsilyl, for example 2,4,6-tri(tert.-butyl)-phenoxydimethylsilyl.

An organic radical $R_3$ ($Y = -S(=O)-R_3$ or $-S(=O)_2-R_3$) is, for example, tert.-lower alkyl, cycloalkyl-lower alkyl, aryl, substituted aryl, or triaryl-lower alkyl, each of which is bonded to the sulphur atom by a carbon atom that is not bonded to hydrogen.

Tert.-lower alkyl $R_3$ is, for example, tert.butyl or tert.-pentyl.

Cycloalkyl-lower alkyl $R_3$ is, for example, 2-cycloalkyl-lower alkyl, for example cycloprop-2-ylprop-2-yl, cyclopent-2-ylprop-2-yl or cyclohex-2-ylprop-2-yl.

Aryl $R_3$ is, for example, phenyl or naphthyl.

Substituted aryl is, for example, phenyl substituted by lower alkoxy, for example methoxy, lower alkyl, for example methyl, nitro and/or by halogen, for example chlorine, for example 4-methoxy- or 4-nitrophenyl, 2-, 3- or 4-chlorophenyl or 4-tolyl.

Triaryl-lower alkyl $R_3$ is, for example, triphenylmethyl.

$R_3$ is preferably tert.-lower alkyl, especially tert.-butyl, or phenyl.

An organic radical $R_3'$ ($Y = -C(=O)-O-R_3'$) is, for example, tert.-lower alkyl, cycloalkyl-lower alkyl, aryl, substituted aryl, or triaryl-lower alkyl having the meanings given hereinbefore, each of which is bonded to the oxygen atom of the carboxy group by a carbon atom that is not bonded to hydrogen.

A carboxy-protecting group $R_3'$ is described in the standard works mentioned under hydroxy-protecting groups $R_2$ and is, for example, an ester group that can be removed selectively under mild conditions, for example lower alkyl, for example methyl or ethyl, arylmethyl having one or two aryl radicals in which aryl preferably represents phenyl that is unsubstituted or mono-, di- or tri-substituted, for example, by lower alkyl, for example tert.-lower alkyl, for example tert.-butyl, lower alkoxy, for example methoxy, hydroxy, halogen, for example chlorine, and/or by nitro, for example benzyl, benzyl substituted by the mentioned substituents, for example 4-nitrobenzyl or 4-methoxybenzyl, diphenylmethyl, or diphenylmethyl substituted by the mentioned substituents, for example di-(4-methoxyphenyl)-methyl, and 1-lower alkoxy-lower alkyl, for example methoxymethyl, 1-methoxyethyl or 1-ethoxymethyl, 1-lower alkylthio-lower alkyl, for example 1-methylthiomethyl or 1-ethylthioethyl, aroylmethoxycarbonyl, for example phenacyloxycarbonyl, and 2-halo-lower alkyl, for example 2,2,2-trichloroethyl, 2-bromoethyl or 2-iodoethyl.

$R_3'$ is preferably tert.-lower alkyl, for example tert.-butyl, phenyl, 4-nitrobenzyl or 4-methoxybenzyl.

An amino-protecting group $R_4'$ is, for example, lower alkoxycarbonyl that is branched in the 1-position of the lower alkyl radical and can be removed by acidolysis, arylmethoxycarbonyl that can be removed by reduction, for example by hydrogenolysis, in which aryl can be substituted by one or two nitro groups, or is preferably arylmethyl or aryl that can be removed by oxidation, in which aryl is preferably substituted by one or two lower alkoxy groups, for example methoxy, and also a 2-lower alkenyl group that can be removed by oxidation.

Lower alkoxycarbonyl $R_4'$ branched in the 1-position of the lower alkyl radical is, for example, tert.-lower alkoxycarbonyl, for example tert.-butoxycarbonyl (BOC). Also suitable are analogous groups, for example tert.-amyloxycarbonyl, isopropoxycarbonyl, cyclohexyloxycarbonyl, d-isobornyloxycarbonyl or adamantyloxycarbonyl.

Arylmethoxycarbonyl $R_4'$, in which aryl can be substituted by one or two nitro groups, is, for example, benzyloxycarbonyl, 4-nitrobenzyloxycarbonyl or 2,4-dinitrobenzyloxycarbonyl.

A lower alkenyl group $R_4'$ that can be removed by oxidation is, for example, allyl.

An amino-protecting group $R_4'$ is preferably arylmethyl or aryl $R_4'$ that can be removed by oxidation, in which aryl is preferably phenyl substituted by one or two lower alkoxy groups, for example by methoxy, especially 4-methoxybenzyl or 2,4-dimethoxybenzyl or 4-methoxyphenyl or 3,4-dimethoxyphenyl.

In a starting material of the formula III, a hydroxy-protecting group $R_2'$ that cannot be removed under the conditions of the cyclisation operation is one of the mentioned acyl groups of a substituted carboxylic or sulphonic acid, for example 2,2,2-trifluoroacetyl, the substituted acyl group of a carbonic acid semiester, for example p-nitrobenzyloxycarbonyl, 2-tetrahydrofuryl or 2-tetrahydropyranyl, or 1-lower alkoxy-lower alkyl, for example methoxymethyl or 1-ethoxyethyl.

In a starting material of the formula III, a suitable nucleofugal group X is, for example, halogen, for example chlorine, bromine or iodine, lower alkanoyloxy, for example acetoxy, arylsulphonyloxy, for example phenylsulphonyloxy or tosyloxy, or lower alkylsulphonyloxy, for example mesyloxy.

A reagent that yields fluoride ions in an aprotic organic solvent is an acid addition salt of hydrogen fluoride with an organic base, for example a tertiary, aliphatic amine, for example tri-n-lower alkylamine, for example triethylamine, an aliphatic, heterocyclic nitrogen base, for example piperidine, 1-ethylpiperidine or morpholine, or a tertiary, aromatic heterocycylic nitrogen base, for example pyridine, collidine or quinoline.

A reagent that yields fluoride ions in an aprotic organic solvent is preferably tetra-lower alkylammonium fluoride, for example tetra-n-butylammonium fluoride.

The cyclisation is carried out in an aprotic organic solvent, for example in an ether, for example diethyl ether, dioxan or tetrahydrofuran, an amide, for example dimethylformamide or hexamethylphosphoric acid triamide, or in a mixture thereof, optionally also in a mixture of the mentioned solvents with an alkane, for example n-hexane or petroleum ether. The reaction temperature is between approximately $-50°$ and $50°$ C., preferably between $-10°$ and room temperature. The operation is preferably carried out under an inert gas atmosphere, for example an argon or nitrogen atmosphere. When using water-containing tetra-n-butylammonium fluoride, the water is removed by a customary drying agent, preferably by the addition to the reaction mixture of freshly activated molecular sieve, for example having a pore diameter of 4 Å.

In the process according to the invention, an inversion of the configuration at the 2-carbon atom of the starting material takes place so that from a 2R-compound of the formula II or III there is formed the 3S-compound of the formula I. The configuration of the 1'-carbon atom ($R_1$=lower alkyl) in the side chain remains unchanged. For example, from R-glycidic acid amides of the formula II there are obtained 3-(S)-azetidinones of the formula I, or from (2R,3R)-2,3-epoxybutyric acid amides of the formula II there are obtained 3-(S)-(1-(R)-hydroxyethyl)azetidinones of the formula I.

If it is intended to manufacture compounds of the formula I in which $R_1$ represents lower alkyl, for example methyl, it is preferable to use compounds of the formula II or III that have the R-configuration at the 2- and at the 3-carbon atom.

The present invention relates preferably to a process for the manufacture of compounds of the formula I in which $R_1$ represents hydrogen or methyl, $R_2$ represents hydrogen or a hydroxy-protecting group, for example the substituted acyl group of a carbonic acid semiester, for example 2,2,2-trichloroethoxycarbonyl, allyloxycarbonyl, benzyloxycarbonyl or p-nitrobenzyloxycarbonyl, or tri-lower alkylsilyl, for example trimethylsilyl or dimethyl-tert.-butylsilyl, Y represents the group —S(=O)$_2$—R$_3$ or —C(=O)—O—R$_3'$ in which $R_3$ or $R_3'$ represents tert.-lower alkyl, for example tert.-butyl, or phenyl, and $R_4$ represents hydrogen or an amino-protecting group $R_4'$, for example 4-methoxybenzyl, 2,4-dimethoxybenzyl, 4-methoxyphenyl or 3,4-dimethoxyphenyl, and in which the 4-carbon atom of the azetidinone ring has the R-configuration if Y represents the group —S(=O)$_2$—R$_3$, and has the S-configuration if Y represents the group —C(=O)—O—R$_3'$, and the 1'-carbon atom of the side chain has the R- or the S-configuration if $R_1$ represents methyl.

In a preferred form of the process, starting materials of the formula II are used in which $R_1$ represents hydrogen or methyl, Y represents the group —S(=O)$_2$—R$_3$ or —C(=O)—O—R$_3'$ in which $R_3$ or $R_3'$ represents tert.-lower alkyl, for example tert.-butyl, or phenyl, and $R_4'$ represents an amino-protecting group, for example 4-methoxybenzyl, 2,4-dimethoxybenzyl, 4-methoxyphenyl or 3,4-dimethoxyphenyl, and the 1'-carbon atom of the side chain has the R- or the S-configuration if $R_1$ represents methyl, which starting materials are optionally manufactured in situ, preferably from compounds of the formula

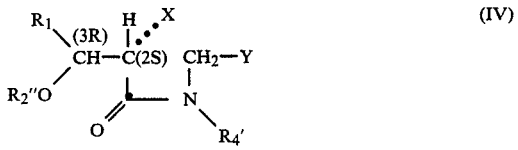

in which Y, $R_1$ and $R_3$ have the meanings indicated, $R_2''$ represents hydrogen or a hydroxy-protecting group that can be removed under the conditions of the epoxide formation, for example a tri-lower alkylsilyl group, $R_4'$ represents an amino-protecting group and X represents a nucleofugal group, and in which the 3-carbon atom has the R-configuration if $R_1$ represents methyl.

In a resulting compound of the formula I, the amino-protecting group $R_4'$ is removed in a manner known per se, for example by solvolysis, for example acidolysis, reduction or oxidation.

Thus, for example, tert.-lower alkoxycarbonyl $R_4'$ can be removed by treatment with a suitable acid, for example formic acid or trifluoroacetic acid, optionally in the presence of water.

Arylmethoxycarbonyl $R_4'$, for example benzyloxycarbonyl, 4-nitrobenzyloxycarbonyl or 2,4-dinitrobenzyloxycarbonyl, can be removed, for example, by treatment with a suitable reducing agent, for example zinc, in the presence of a carboxylic acid, for example acetic acid.

An arylmethyl group $R_4'$, for example 4-methoxy-or 2,4-dimethoxy-benzyl, is removed, for example, by oxidation, for example by reaction with a strong oxidising agent, for example an inorganic peroxide salt, for example sodium or potassium peroxydisulphate, in the presence of an acidic salt, for example dipotassium hydrogen phosphate, and optionally in the presence of a catalyst, for example a metal salt, for example an iron(II) and/or copper(II) salt, for example iron(II) sulphate heptahydrate and/or copper(II) acetate hydrate, or preferably by oxidation by reaction with a cerium(IV) salt, for example cerium(IV) iodate, cerium(IV) nitrate (CeOH(NO$_3$)$_3$), cerium(IV) sulphate or, preferably, diammonium cerium(IV) hexanitrate, in the presence of an acid, for example aqueous HCl, and subsequent reaction with a reducing agent, for example sodium bisulphite.

An aryl group $R_4'$, for example 4-methoxyphenyl or 3,4-dimethoxyphenyl, and also the lower alkenyl group, is preferably removed by oxidation, for example by ozonolysis in ethyl acetate, and subsequent decomposition of the ozonides formed by reduction with a reducing agent, for example sodium thiosulphate, or by reaction with a cerium(IV) salt, for example diammonium cerium(IV) hexanitrate, and subsequent reduction.

The described cleavage reactions are carried out under conditions known per se, if necessary while cooling or heating and optionally under an inert gas atmosphere, for example a nitrogen atmosphere.

A hydroxy-protecting group $R_2$ can be introduced in a manner known per se, for example by reaction of a compound of the formula I in which $R_2$ represents hydrogen with a reactive derivative of an acid of which the acyl group is the hydroxy-protecting group, for example by reaction with an anhydride, for example trifluoroacetic acid anhydride, a mixed anhydride, for example an acid halide, for example 2,2-dichloroacetyl chloride, an anhydride of a carbonic acid semiester, for example 2,2,2-trichloroethoxy-, phenyl- or p-nitrophenylchloroformate, by reaction with 1,2-dihydrofuran or 1,2-dihydropyran in the presence of an acid, for example p-toluenesulphonic acid, or by reaction with a tri-lower alkylhalosilane, for example trimethylchloro- or dimethyl-tert.-butylchloro-silane.

A resulting compound of the formula I in which Y represents the group —S(=O)—R$_3$ can be converted into the corresponding compound of the formula I in which Y represents the group —S(=O)$_2$—R$_3$, for example using a suitable oxidising agent.

A suitable oxidising agent is, for example, hydrogen peroxide, a peracid, for example an aliphatic or aromatic peracid, for example peracetic acid, perbenzoic acid or m-chloroperbenzoic acid, as well as anodic oxidation, for example on a platinum electrode, in acidic solution, for example in a solution containing sulphuric acid. The oxidation is preferably carried out in a suitable inert solvent, for example in a halogenated hydrocarbon, for example methylene chloride or chloroform, an alcohol, for example methanol or ethanol, a ketone, for example acetone, an ether, for example diethyl ether, dioxan or tetrahydrofuran, a liquid organic carboxylic acid, for example acetic acid, or in an aqueous mixture of these solvents, at room temperature, while cooling or heating, for example at from approximately −20° C. to approximately +90° C., preferably at from −20° C. to approximately 30° C.

The further processing of compounds of the formula I ($R_4$=H) is effected in a manner known per se and, depending upon the meaning of Y, results in (5R,6S)-penem-3-carboxylic acids or (5R,6S)-carbapenems having valuable pharmacological, for example antibacterial, properties.

The further processing of a compound of the formula I in which Y represents the group —C(=O)—O—$R_3'$ and $R_4'$ represents an amino-protecting group, can be effected in two different ways. First of all the amino-protecting group $R_4'$, for example p-methoxybenzyl, can be removed, for example as described hereinbefore by oxidation with cerium(IV)-ammonium nitrate, and then the group Y can be converted by customary cleaving of the ester group into the free carboxylic acid —C(=O)—OH, for example by the action of trifluoroacetic acid, and this carboxylic acid can be converted by oxidation with lead(IV) acetate in an inert solvent into an azetidinone that is substituted in the 4-position by acetoxy.

It is also possible to carry out the reaction steps in reverse order by first removing the ester group $R_3'$ and reacting oxidatively the free carboxylic acid with lead-(IV) acetate, with the removal of $CO_2$, to form the 4-acetoxy compound which is obtained selectively in the trans-form. In a further step, the amino-protecting group $R_4'$ is removed as described with cerium(IV) ammonium nitrate. Azetidinones that are substituted in the 4-position by acetoxy can be further processed subsequently to form penems or carbapenems.

The manufacture of the starting materials of the formulae II and III is effected in a manner known per se, for example analogously to the processes described by Yanagisawa H. et al. or Shiozaki M. et al.

For example, in a compound of the formula IV in which Y, $R_1$ and $R_3$ have the meanings given under formula I, $R_2''$ represents hydrogen or a hydroxy-protecting group that can be removed under the conditions of the epoxide formation, $R_4'$ represents an amino-protecting group and X represents a nucleofugal group, the acid HX can be removed, and a resulting compound in which Y represents the group —S—$R_3$ can be converted into a compound in which Y represents the group C(=O)—O—$R_3$ or —$SO_2$—$R_3$.

In a compound of the formula IV, a hydroxy-protecting group $R_2''$ that can be removed under the conditions of the epoxide formation is a tri-lower alkylsilyl group, for example dimethyl-tert.-butylsilyl or trimethylsilyl, and X preferably represents halogen, for example chlorine or bromine, lower alkylsulphonyloxy, for example mesyloxy, or arylsulphonyloxy, for example tosyloxy.

The removal of HX is effected using one of the bases mentioned under process (b), for example sodium or potassium hydroxide or sodium or potassium carbonate, preferably using an amidine, for example 1,5-diazabicyclo[5.4.0]undec-5-ene, or using a tetra-lower alkylammonium fluoride, for example dehydrated tetra-n-butylammonium fluoride.

The reaction to form an epoxy compound of the formula II is preferably carried out in an inert, preferably anhydrous, solvent or solvent mixture, for example in a carboxylic acid amide, for example dimethylformamide, a halogenated hydrocarbon, for example methylene chloride, chloroform, carbon tetrachloride or chlorobenzene, a ketone, for example acetone, cyclic ethers, for example dioxan or tetrahydrofuran, an ester, for example ethyl acetate, or a nitrile, for example acetonitrile, or in mixtures thereof, optionally at reduced or elevated temperature, for example in a temperature range of from approximately −40° C. to approximately +100° C., preferably from approximately −10° C. to approximately 50° C., and optionally under an inert gas atmosphere, for example a nitrogen atmosphere.

In the reaction according to process (c), the configuration of the 2-carbon atom is reversed, whereas the configuration of the 3-carbon atom ($R_1$ = lower alkyl) is retained. The (2R,3R)-compounds of the formula II are formed from 2-(S)-halogen-3-(R)-hydroxycarboxylic acid amides of the formula IV. The same applies to the 2-(S)-halogen-3-(S)-hydroxycarboxylic acid amides of the formula II.

The conversion of a compound of the formula IV into the epoxy compound of the formula II is effected in a manner known per se, for example under the reaction conditions known from steroid chemistry, see Djerassi C. et al., "Steroid Reactions" Holden Day, San Francisco 1963, pages 606–613.

Compounds of the formula IV can be manufactured, for example, by amidation of a carboxylic acid of the formula

in which $R_1$ has the meaning given under formula I and $R_2''$ has the meaning given under formula IV and X represents a nucleofugal group, with an amine of the formula $$R_4'NH—CH_2—Y' \qquad (VI),$$

in which Y' represents the group —S—$R_3$, —S(=O)—$R_3$, —S(=O)$_2$—$R_3$ or —C(=O)—O—$R_3'$, and $R_4'$ represents an amino-protecting group, or by condensation of an amide of the formula

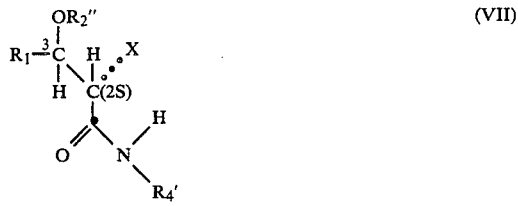

in which $R_1$ has the meaning given under formula I and $R_2''$ has the meaning given under formula IV, X represents a nucleofugal leaving group and $R_4'$ represents a suitable amino-protecting group, with a halide of the formula $$Z—CH_2—Y' \qquad (VIII)$$

in which Z represents halogen, for example chlorine, bromine or iodine, and, optionally, oxidation of the group —S—$R_3$.

Compounds of the formula V are known. They can be manufactured, for example, in a manner known per se from L-serine or L-threonine by diazotisation of the amino group with a nitrite salt, for example potassium nitrite, and reaction of the resulting diazo compound with a bromide salt, for example potassium bromide.

When using L-serine, according to the described processes it is possible, starting from compounds of the formula V, to obtain compounds of the formula I in which the carbon atom in the 3-position of the azetidinone ring has the S-configuration.

When using L-threonine, compounds of the formula I are obtained in which the carbon atom in the 3-position of the azetidinone ring has the S-configuration and the 1'-carbon atom of the hydroxyethyl side chain has the R-configuration. If it is intended to manufacture compounds of the formula I in which the 3-carbon atom has the S-configuration and the 1'-carbon atom of the hydroxyethyl side chain has the R-configuration, allo-threonine is used as starting material. In all the reactions described, the configuration of the carbon atom that in compounds of the formula I corresponds to the 1'-carbon atom of the 3-lower alkyl-CH-(OR$_2$)-side chain remains unchanged.

Compounds of the formula VII are known or, if they are novel, can be manufactured in a manner known per se according to the instructions of Reynolds D. D. and Cossar B. C., J. Heterocycl. Chem. 8, 597 (1971).

The present invention relates also to those forms of the process in which a compound obtainable at any preliminary stage of the process is used as starting material and the remaining process steps are carried out. p The following Examples serve to illustrate the invention. Temperatures are given in degrees Centigrade and IR values in cm$^{-1}$. For the $^1$H-HMR spectra, the chemical shifts (δ) are given in ppm and the coupling constants J in Herz (Hz). The specific rotation values [α] are [α]$_D^{20}$ values. For chromatographic separation in the case of preparative working up, columns filled with Merck silica gel 60 are used. R$_f$ values apply to precoated plates for thin layer chromatography (Merck 60 F 254).

Abbreviations:
m = medium strength absorption bands
sh = sharp absorption bands
S = singlet
M = multiplet
D = doublet
m.p. = melting point
b.p. = boiling point Example 1: benzyl-tert.-butylthiomethylammonium chloride The compound is prepared as follows, analogously to a general method of D. D. Reynolds and B. C. Cossar, J. Heterocycl. Chem. 8, 597 (1971):

There results from the addition of 1.19 g (3.33 mmol) of 1,3,5-tribenzylhexahydro-1,3,5-triazine in 5 ml of diethyl ether to 15 ml of a solution of 0.40 g of hydrogen chloride in ether at −20° a suspension of a white crystalline precipitate to which 1.19 ml (10.5 mmol) of tert.-butylmercaptan are then added at the same temperature. Stirring is continued at room temperature with the exclusion of moisture, the original crystals temporarily agglomerating and new white crystals of the title compound being formed. After stirring for 4 hours, the latter are filtered with suction, washed with a little diethyl ether and dried in vacuo.

M.p. 107° (conversion to form new crystals; completely molten at 142°.

The starting material 1,3,5-tribenzylhexahydro1,3,5-triazine may also be prepared according to D. D. Reynolds and B. C. Cossar, loc. cit. This compound has the following characteristic data: IR (in CH$_2$Cl$_2$) 3080-2600 (m), 1600, 1490, 1450, 1360, 1340 (sh), 1312, 1168, 1117, 1071, 1030, 1016, 980, 920;

$^1$H-NMR (60 MHz, in CDCl$_3$): δ=3.48 (S, 2H), 3.70 (S, 2H), 7.36 (M, 5H).

Example 2:
N-benzyl-N-tert.-butylthiomethyl-2-(S)-bromo-3-hydroxypropionic acid amide Under an argon atmosphere, 202 mg (2 mmol) of triethylamine and 413 mg (2 mmol) of dicyclohexyl carbodiimide are added while stirring, at room temperature, to a mixture of 338 mg (2 mmol) of 2-(S)-bromo-3-hydroxypropionic acid and 492 mg. (2 mmol) of N-benzyl-N-tert.butylthiomethylammonium chloride in 10 ml of absolute tetrahydrofuran and the resulting reaction mixture is stirred for a further 2 hours at room temperature. The dicyclohexylurea that has precipitated is filtered off with suction and then washed with a little THF. The combined filtrates are concentrated by evaporation under reduced pressure and the oily residue is chromatographed over a silica gel column using toluene: ethyl acetate (9:1). After the first fractions, which contain small amounts of N,N-bis-(tert.-butylthiomethyl)-benzylamine, have been removed, the title compound is eluted in the form of a colourless oil that crystallises slowly on standing.

M.p. 65°-68° (from hexane); R$_f$(toluene: ethyl acetate 1:1): 0.56.

The $^1$H-NMR spectrum (in CDCl$_3$ and in D$_6$-benzene) indicates the presence of two rotamers (2 groups of signals).

The known starting material 2-(S)-bromo-3-hydroxypropionic acid may be prepared according to the method of U. Shimohigashi, M. Waki and N. Izumiya, Chem. Abstr. 91, 39804 u (1979).

Example 3:
N-benzyl-N-tert.-butylsulphinylmethyl-2-(S)-bromo-3-hydroxypropionic acid amide 48 mg (approximately 0.25 mmol) of 90% m-chloroperbenzoic acid dissolved in 5 ml of methylene chloride are added slowly at −20° to a solution of 90 mg (0.25 mmol) of N-benzyl-N-tert.-butylthiomethyl-2-(S)-bromo-3-hydroxypropionic acid amide in 5 ml of methylene chloride and the resulting reaction mixture is stirred for a further one hour at −20°. After washing with a 5% aqueous NaHCO$_3$ solution, the organic layer is dried over anhydrous Na$_2$SO$_4$ and concentrated by evaporation. The oily residue contains the title compound in the form of two isomeric S-oxides.

R$_f$ (toluene/ethyl acetate 1:1) : 0.13-0.20 (overlapping);
IR (CH$_2$Cl$_2$): 3560-3250, 2950, 1654, 1495, 1470-1390, 1362, 1230-1140, 1040, 910.

Example 4:
N-benzyl-N-tert.-butylsulphonylmethyl-2-(S)-bromo-3-hydroxypropionic acid amide While stirring at −10°, a total of 4.03 g (approximately 21 mmol) of 90% m-chloroperbenzoic acid is added in several portions in the course of 15 minutes to a solution of 3.44 g (9.56 mmol) of N-benzyl-N-tert.-butylthiomethyl-2-(S)-bromo-3-hydroxypropionic acid amide in 75 ml of methylene chloride. After stirring for a further one hour at 0°, the reaction mixture is diluted with 100 ml of methylene choride and washed in succession with 75 ml of a 2% aqueous NaHSO$_3$ solution and 75 ml of an 8% aqueous NaHCO$_3$ solution. The aqueous portions are then extracted with 50 ml of methylene chloride. After drying of the combined organic phases over sodium sulphate and concentration by evaporation in vacuo, the title compound remains in the form of a virtually colourless oil.

$R_f$(toluene: ethyl acetate 1:1): 0.36;
IR ($CH_2Cl_2$) 3600–3350, 3000–2850, 1661, 1494, 1475 (sh), 1450, 1420, 1395, 1352, 1300, 1250 (sh), 1220, 1197, 1173, 1140, 1110, 1035, 880.

Example 5:
N-benzyl-N-tert.-butylthiomethyl-(R)-glycidic acid amide 5 ml of a 2M solution of 1,5-diazabicyclo[5.4.0]-undec-5-ene (DBU) in tetrahydrofuran are added while stirring, at room temperature, to a solution of 845 mg (5 mmol) of 2-(S)-bromo-3-hydroxypropionic acid in 10 ml of absolute tetrahydrofuran and the resulting mixture is stirred for a further 2 hours at room temperature. The solvent is subsequently distilled off in vacuo and 25 ml of methylene chloride are added. To this solution containing the DBU salt of (R)-glycidic acid there are added 1.03 g (5 mmol) of dicyclohexyl carbodiimide and, after stirring for one hour, 1.3 g (5 mmol) of N-benzyl-N-tert.-butylthiomethylammonium chloride. After the addition of the last-mentioned reaction component, crystalline dicyclohexylurea is formed. After a reaction time of 3 hours at room temperature, the latter is filtered off with suction and the filtrate is diluted with methylene chloride and washed with phosphate buffer solution having a pH of 8. After concentration of the organic phase by evaporation, the residue is chromatographed over 50 g of silica gel. After a few first fractions have been removed with toluene, the title compound is eluted with a mixture of toluene/ethyl acetate (9:1) in the form of a colourless, viscous oil.

$R_f$ (toluene: ethyl acetate 1:1): 0.45; $[\alpha] = +24 \pm 1°$ (1.12% in chloroform).

The $^1$H-NMR spectrum (in CDCl$_3$) has two groups of signals which correspond to two rotamers in a ratio of approximately 2:1.

Example 6:
N-benzyl-N-tert.-butylsulphonylmethyl-(R)-glycidic acid amide

A total of 1.37 g (approximately 7.12 mmol) of 90% m-chloroperbenzoic acid is added in several portions at -10° to a solution of 910 mg (3.26 mmol) of N-benzyl-N-tert.-butylthiomethyl-(R)-glycidic acid amide in 30 ml of methylene chloride and the resulting mixture is stirred for a further 90 minutes at 0°. A little $CH_2Cl_2$ is then added to the reaction mixture and the whole is washed in succession with cold, aqueous 2% sodium bisulphite solution. The crude product contained in the $CH_2Cl_2$ phase is chromatographed over 50 g of silica gel. The crystalline title compound is eluted with a mixture of toluene/ethyl acetate (1:1).

M.p. 106°–107° (from methylene chloride/diethyl ether);

($R_f$ toluene: ethyl acetate 1:1): 0.29; $[\alpha] = +24 \pm 1°$ (1.31% in CHCl$_3$).

$^1$H-NMR spectrum (in CDCl$_3$): 2 groups of signals indicate 2 rotamers in a ratio of approximately 4:1).

Example 7:
N-benzyl-N-tert.-butylsulphonylmethyl-(R)-glycidic acid amide 1.125 g (7.4 mmol) of 1,5-diazabicyclo[5.4.0]undec-5-ene are added at 0° to a solution of 118 g (3 mmol) of N-benzyl-N-tert.-butylsulphonylmethyl-2-(S)-bromo-3-hydroxypropionic acid amide (see Example 4) in 15 ml of absolute tetrahydrofuran and the whole is stirred for a further 90 minutes at room temperature. After working up with methylene chloride and phosphate buffer having a pH of 7.0, the crude product obtained from the organic phase is chromatographed over 50 g of silica gel. After eluting with a mixture of ethyl acetate/toluene (1:1), the pure title compound, identical to the compound according to Example 6, is obtained.

Example 8:
1-benzyl-(3)-S-hydroxymethyl-4-(R)-tert.butylsulphonyl-2-azetidinone (a) 3 ml of a tetra-n-butylammonium fluoride solution which has been prepared from 5.0 g of tetra-n-butylammonium fluoride trihydrate (Fluka) by drying at 60°/0.1 torr and making up to 20 ml with absolute tetrahydrofuran are added at 0° to a solution of 103.9 mg (0.333 mmol) of N-benzyl-N-tert.butylsulphonylmethyl-R-glycidic acid amide in 0.5 ml of absolute tetrahydrofuran. After stirring for one hour at 0°, the reaction mixture is taken up in a 5:1 mixture of diethyl ether and methylene chloride and washed with aqueous phosphate buffer having a pH of 8.0. After drying of the organic phase with anhydrous sodium sulphate and concentration by evaporation in vacuo, the pure title compound is obtained by triturating with a little ether.

M.p. 139°–141°; $R_f$(ethyl acetate: hexane 2:1); 0.17; $[\alpha] = +35 \pm 1°$ (1.30% in CHCl$_3$);

$^1$H-NMR spectrum: $\delta = 4.71$ (D) for proton (a) at the 4-(R)-carbon atom and $\delta = 3.75$ (M) for proton (b) at the 3-(S)-carbon atom (trans-compound), J a-b: approximately 2.

(b) 5.9 ml of a solution prepared from 5 g of tetra-n-butylammonium fluoride trihydrate by dehydrating at 55°–60°/0.1 mm and dissolving in 20 ml of tetrahydrofuran are added to a solution of 196 mg (0.5 mmol) of N-benzyl-N-tert.-butylsulphonylmethyl-2-(S)-bromo-3-hydroxypropionic acid amide (Example 4) in 0.8 ml of tetrahydrofuran. The resulting reaction mixture is stirred for two hours at +5° after the addition of activated molecular sieve (type 4A 1/16, Messrs. Dr. Bender & Dr. Hobein). The molecular sieve is filtered off with suction and washed with methylene chloride. The combined filtrates are diluted with ether and washed with phosphate buffer having a pH of 8. After drying of the organic phase over sodium sulphate and concentration by evaporation under reduced pressure, a crude product remains which produces the crystalline title compound by means of chromatography over preparative silica gel plates using hexane/ethyl acetate (1:3).

Example 9: N-allyl-N-tert.butylthiomethylammonium chloride

The title compound is prepared as follows, analogously to a general method of D. D. Reynolds and B. C. Cossar, J. Heterocycl. Chem. 8, 597 (1971):

A solution of 18.65 g (0.09 mol) of 1,3,5-triallylhexahydro-1,3,5-triazine in 175 ml of ether is added dropwise at -20° to a solution of 10.8 g (0.3 mol) of hydrogen chloride in 100 ml of ether, 30.6 ml (0.27 mol) of tert.-butylmercaptan are added to the resulting suspension and the mixture is stirred for a further 18 hours at room temperature.

The precipitated white crystals are filtered off with suction, washed with ether and recrystallised from methylene chloride/ether. White crystals of the title compound, having a melting point of 85°–90°, are obtained.

The starting material 1,3,5-triallylhexahydro-1,3,5-triazine can be prepared in accordance with the method of D. D. Reynolds and B. C. Cossar (J. Heterocycl. Chem. 8, 597 (1971)): b.p. 67°–70°/1.8 mbar (Reynolds and Cossar: b.p. 92°/0.4 mm).

Example 10:
N-allyl-N-tert.-butylthiomethyl-(R)-glycidic acid amide

Analogously to Example 5, the DBU salt of (R)-glycidic acid is prepared in situ from 845 mg (5 mmol) of 2-(S)-bromo-3-hydroxypropionic acid in tetrahydrofuran with 10 mmol of 1,5-diazabicyclo[5.4.0]undec-5-ene, the DBU salt is treated in methylene chloride with 1.03 g (5 mmol) of dicyclohexyl carbodiimide and 979 mg (5 mmol) of allyl-tert.-butylthiomethylammonium chloride and the resulting crude product is chromatographed over silica gel in mixtures of hexane and ethyl acetate (9:1) and (4:1). The title compound is obtained in the form of a colourless oil.

$R_f$(toluene: ethyl acetate 1:1): 0.40;
IR ($CH_2Cl_2$) 3080–2850, 1660, 1458, 1440 (sh), 1410, 1360, 1300–1240, 1220 (sh), 1208, 1160, 980, 940, 910, 890.

Example 11:
N-allyl-N-tert.-butylsulphonylmethyl-(R)-glycidic acid amide

In the course of 15 minutes, 1.05 g (approximately 5.5 mmol) of 90% m-chloroperbenzoic acid are added in several portions at −10° to a solution of 573 mg (2.5 mmol) of N-allyl-N-tert.-butylthiomethyl-(R)-glycidic acid amide in 20 ml of methylene chloride and the mixture is stirred for 2 hours at 0°. The whole is then diluted with methylene chloride and washed in succession with ice-cold 2% aqueous sodium bisulphite solution and ice-cold 5% aqueous sodium bicarbonate solution. The aqueous portions are then extracted with methylene chloride, the combined $CH_2Cl_2$ extracts are dried over sodium sulphate and concentrated by evaporation and the resulting oily residue is chromatographed over silica gel using toluene/ethyl acetate (4:1). The title compound is obtained in the form of a colourless oil.

$R_f$ (toluene: ethyl acetate 4:1): 0.22; $[\alpha] = +44 \pm 1°$ (1.55% in $CHCl_3$).

Example 12:
1-allyl-3-(S)-hydroxymethyl-4-(R)-tert.-butylsulphonyl-2-azetidinone A solution of 197 mg (0.757 mmol) of N-allyl-N-tert.-butylsulphonylmethyl-(R)-glycidic acid amide in 1 ml of tetrahydrofuran is introduced at 0°, with the exclusion of moisture, into 8 ml of a tetra-n-butyl; ammonium fluoride/THF solution which has been prepared from 5.0 g of tetra-n-butylammonium fluoride trihydrate by dehydrating at 60° C./0.1 torr and making up to 20 ml with tetrahydrofuran. The reaction mixture is stirred for 2 hours at room temperature and then partitioned between methylene chloride and phosphate buffer solution (pH 8.0). The crude product obtained by drying over sodium sulphate and concentration by evaporation of the organic phase is chromatographed over preparative silica gel plates using hexane/ethyl acetate (1:3). the title compound is obtained in the form of colourless crystals.

M.p. 99°–103°;

$R_f$ (hexane/ethyl acetate 1:3): 0.18; $[\alpha] = 46 \pm 1°$ (1.30% in $CHCl_3$);

$^1$H-NMR spectrum: $\delta = 4.96$ for proton (a) at the 4-(R)-carbon atom and $\delta = 3.72$ for proton (b) at the 3-(S)-carbon atom (trans-compound), J a-b: approximately 2.

Example 13: N-allyl-N-phenylthiomethylammonium chloride is prepared as follows, according to the general method of D. D. Reynolds and B. C. Cossar, loc. cit.

A solution of 20.73 g (0.1 mol) of 1,3,5-triallylhexahydro-1,3,5-triazine in 150 ml of diethyl ether is added dropwise at −20° to a solution of 12 g of hydrogen chloride in 130 ml of diethyl ether and the resulting suspension of white crystals is stirred for a further 15 minutes at that temperature. 30.6 ml (0.3 mol) of thiophenol are then added thereto in one portion and the reaction mixture is stirred for 20 hours at room temperature. The crystals of the title compound that are formed are filtered off with suction and washed on the filter with diethyl ether.

M.p. 100°.

Example 14: N-allyl-N-phenylthiomethyl-(R)-glycidic acid amide

Analogously to Example 5, 8.45 g (50 mmol) of 2-(S)-bromo-3-hydroxypropionic acid in 200 ml of tetrahydrofuran is converted using 15.2 g (100 mmol) of 1,5-diazabicyclo[5.4.0]undec-5-ene into the DBU salt of (R)-glycidic acid. To the latter there are added in situ in methylene chloride at room temperature, 10.31 g (50 mmol) of dicyclohexyl carbodiimide and then, at 0°, 10.75 g (50 mmol) of N-allyl-N-phenylthiomethylammonium chloride. The resulting mixture is stirred for a further 3 hours at room temperature. The crystalline dicyclohexylurea is filtered off with suction, methylene chloride is added to the filtrate and the whole is washed with phosphate buffer having a pH of 8.0. The crude product obtained from the organic phase by drying over sodium sulphate and concentration by evaporation in vacuo is chromatographed over 500 g of silica gel using toluene/ethyl acetate (9:1) and the pure title compound is obtained in the form of a colourless oil.

$R_f$(toluene: ethyl acetate 1:1): 0.39;
IR ($CH_2Cl_2$): 3050–2850, 1660, 1500, 1446, 1405, 1360, 1340, 1201, 1080, 1020, 990, 907, 892.

Example 15:
N-allyl-N-phenylsulphonylmethyl-(R)-glycidic acid amide

A solution of 1.99 g (8.52 mmol) of N-allyl-N-phenylthiomethyl-(R)-glycidic acid amide in 75 ml of methylene chloride is stirred for 2 hours at 0° with 3.59 g (approximately 18.7 mmol) of 90% m-chloroperbenzoic acid and the resulting reaction mixture, after being diluted with methylene chloride, is washed with 2% ice-cold aqueous sodium bisulphite solution and with 5% ice-cold aqueous sodium bicarbonate solution. The crude product obtained from the organic phase by concentrating by evaporation in vacuo is crystallised from methylene chloride/diethyl ether and the pure title compound is obtained in the form of white crystals. A further portion of pure title compound is obtained by chromatography of the mother liquor residue over silica gel using toluene: ethyl acetate 9:1.

m.p. 82°–84°;

$R_f$ (toluene: ethyl acetate 1:1): 0.23; $[\alpha] = 22 \pm 1°$ (1.02% in CHCl$_3$).

The $^1$H-NMR spectrum (in CDCl$_3$, 400 MHz) shows a doubling of signals and indicates the existence of two rotamers.

Example 16:
1-allyl-3-(S)-hydroxymethyl-4-(R)-phenylsulphonyl-2-azetidinone 8 ml of a tetra-n-butylammonium fluoride/THF solution which has been prepared from 5 g of tetra-n-butylammonium fluoride trihydrate by drying at 60°/0.1 torr and making up to 20.0 ml with tetrahydrofuran is added to a solution of 201 mg (0.757 mmol) of N-allyl-N-phenylsulphonylmethyl-(R)-glycidic acid amide in 1 ml of tetrahydrofuran. The resulting reaction mixture is stirred for 2 hours at 0° and then partitioned between methylene chloride and phosphate buffer solution having a pH of 8.0. The crude product isolated from the organic layer by means of concentration by evaporation over preparative silica gel plates in ethyl acetate/hexane (2:1) and the title compound is obtained in the form of a colourless oil.

$R_f$(hexane: ethyl acetate 1:2): 0.19;

IR (CH$_2$Cl$_2$) 3600–3250 (with a maximum at 3590), 3050, 2910, 2850, 1763, 1440, 1375, 1320, 1305, 1250 (sh), 1145, 1082, 1032, 940;

NMR spectrum: $\delta = 4.83$ for proton (a) at the 4-(R)-carbon atom and $\delta = 3.52$ for proton (b) at the 3-(S)-carbon atom (trans-compound), J a-b: approximately 2.

Example 17:
2,4-dimethoxybenzyl-tert.-butylthiomethylammonium chloride

A solution of 895 mg (1.67 mmol) of 1,3,5-tris-(2,4-dimethoxybenzyl)-hexahydro-1,3,5-triazine in 10 ml of acetonitrile is added dropwise at −25° to a solution of 202 mg of hydrogen chloride in 4 ml of acetonitrile and the resulting reaction mixture is stirred for a further 15 minutes at that temperature. After the addition of 0.567 ml (5 mmol) of tert.-butylmercaptan, stirring of the mixture is continued overnight at room temperature. After concentration by evaporation under reduced pressure, taking up with methylene chloride and concentration by evaporation again, the crude title compound is obtained in the form of a foam. This is used in the next stage without further purification.

The 1,3,5-tris-(2,4-dimethoxybenzyl)-hexahydro-1,3,5-triazine used as starting material may be prepared according to the general method of D. D. Reynolds and B. C. Cossar, loc. cit;

$^1$H-NMR spectrum (in CDCl$_3$ 60 MHz): 3.53 (S, 2H); 3.73 (S, 2H); 3.86 (broad S, 6H; 2 OCH$_3$); 6.36–6.64 (M, 2H); 7.20–7.50 (M, 1H).

Example 18:
N-2,4-dimethoxybenzyl-N-tert.-butylthiomethyl-(R)-glycidic acid amide Analogously to Example 5, 7.605 g (45 mmol) of 2-(S)-bromo-3-hydroxypropionic acid are converted with 13.7 g (90 mmol) of 1,5-diazabicyclo[5.4.0]undec-5-ene in tetrahydrofuran into the DBU salt of (R)-glycidic acid. To the latter there are added in situ in methylene chloride at room temperature, 9.28 g (45 mmol) of dicyclohexyl carbodiimide and 45 mmol of 2,4-dimethoxybenzyl-tert.-butylthiomethylammonium chloride. The dicyclohexylurea formed is filtered off with suction and the filtrate is partitioned between methylene chloride and phosphate buffer solution having a pH of 8.0. After chromatography of the residue and concentration by evaporation of the organic phase over a 1000 g silica gel medium pressure column using toluene/ethyl acetate (9:1), the pure title compound is obtained in the form of a viscous oil.

$R_f$(toluene: ethyl acetate 1:1) 0.42;

IR (CH$_2$Cl$_2$) 3050 (sh), 2930, 2800, 1660, 1605, 1580, 1500, 1450, 1360, 1287, 1250 (sh), 1205, 1158, 1126, 1030.

Example 19:
N-2,4-dimethoxybenzyl-N-tert.-butylsulphonylmethyl-(R)-glycidic acid amide 6.08 g (approximately 31.75 mmol) of 90% m-chloroperbenzoic acid are added at −10° to a solution of 492 g (14.43 mmol) of N-2,4-dimethoxybenzyl-N-tert.-butylthiomethyl-(R)-glycidic acid amide in 120 ml of methylene chloride and the whole is then stirred for two hours at 0°. The resulting reaction mixture is washed, after being diluted with methylene chloride, in succession with 2% aqueous sodium bisulphite solution and 5% aqueous sodium bicarbonate solution. The resulting residue is chromatographed in vacuo, after concentration by evaporation of the organic phase, over 300 g of silica gel in toluene/ethyl acetate (4:1) and the title compound is obtained in the form of a colourless, viscous oil.

$R_f$(toluene: ethyl acetate 1:1): 0.23;

IR (CH$_2$Cl$_2$) 3050–2880, 1662, 1608, 1585, 1502, 1460, 1452 (sh), 1437, 1360, 1250 (sh), 1208, 1160, 1130, 1112, 1030.

The $^1$H-NMR spectrum (in CDCl$_3$, 360 MHz) indicates the existence of a principal rotamer.

The title compound may also be prepared in situ from 2-(S)-bromo-3-hydroxypropionic acid and 2,4-dimethoxybenzyl-tert.-butylthiomethylammonium chloride, without isolating N-2,4-dimethoxybenzyl-N-tert.-butylthiomethyl-(R)-glycidic acid amide.

Example 20:
1-(2,4-dimethoxybenzyl)-3-(S)-hydroxymethyl-4-(R)-tert.-butylsulphonyl-2-azetidinone To a solution of 3.35 g (9.0 mmol) of N-2,4-dimethoxybenzyl-N-tert.-butylsulphonylmethyl-(R)-glycidic acid amide in 14 ml of tetrahydrofuran there are added at 0°, with the exclusion of moisture, 53 ml of a solution of tetra-n-butylammonium fluoride in THF which has been prepared from 20 g of tetra-n-butylammonium fluoride trihydrate (Fluka) by dehydrating at 60°/0.1 torr and making up to 80 ml with tetrahydrofuran. 50 g of molecular sieve freshly activated at 0.1 torr (type 4A 1/16, Messrs. Dr. Bender & Dr. Hobein) are added to the reaction mixture and the whole is stirred for 2 hours at 0°. The molecular sieve is filtered off and washed with 360 ml of methylene chloride and the combined filtrates are washed, after the addition of 1.8 liters of diethyl ether, with 200 ml of a phosphate buffer solution having a pH of 8.0. After distilling off the organic solvent, the residue is chromatographed over 110 g of silica gel using toluene/ethyl acetate (2:1) and (1:1). The title compound is obtained which, after recrystallisation from methylene chloride/ether/pentane, forms white crystals.

M.p. 124°–125°; $[\alpha] = +10 \pm 1°$ (1.09% in CHCl$_3$);

$^1$H-NMR spectrum: $\delta = 4.61$ for proton (a) at the 4-(R)-carbon atom and $\delta = 3.69$ for proton (b) at the 3-(S)-carbon atom (trans-compound), J a-b: approximately 2.

Example 21:
1-(2,4-dimethoxybenzyl)-3-(S)-dimethyl-tert.-butyl-silyloxymethyl-4-(R)-tert.-butylsulphonyl-2-azetidinone A solution of 870 mg (2,34 mmol) of 1-(2,4-dimethoxybenzyl)-3-(S)-hydroxymethyl-4-(R)-tert.-butylsulphonyl-2-azetidinone, 706 mg (4.86 mmol) of tert.-butyldimethylchlorosilane and 318 mg (4.68 mmol) of imidazole in 8 ml of dimethylformamide is stirred for 1.5 hours at room temperature and concentrated by evaporation under a high vacuum at 25°. The residue is taken up in ethyl acetate and washed in succession with water, 8% aqueous NaHCO$_3$ solution and again with water, all aqueous portions subsequently being extracted with ethyl acetate. The combined organic phases are dried over Na$_2$SO$_4$ and concentrated by evaporation under reduced pressure and the resulting residue is chromatographed over 30 g of Merck silica gel using toluene: ethyl acetate (4:1). The crystalline title compound is obtained.

M.p. 113°–114° (from CH$_2$Cl$_2$-Et$_2$O-pentane);

R$_f$ (ethyl acetate: hexane 3:1): 0.61; [α= −6 ±1° (1.10% in CHCl$_3$).

Example 22:
3-(S)-dimethyl-tert.-butylsilyloxymethyl-4-(R)-tert.-butylsulphonyl-2-azetidinone (a) A solution of 97 mg (0.2 mmol) of 1-(2,4-dimethoxybenzyl)-3-(S)-dimethyl-tert.-butylsilyloxymethyl-4-(R)-tert.-butylsulphonyl-2-azetidinone, 486 mg (1.8 mmol), of potassium peroxydisulphate and 174 mg (1.0 mmol) of dipotassium hydrogen phosphate in 4 ml of water and 4 ml of acetonitrile is heated for 3.5 hours at 65°. The solvent is distilled off under reduced pressure and the aqueous residue is extracted with ethyl acetate. The resulting crude product is chromatographed over preparative silica gel plates using toluene/ethyl acetate (4:1) and the title compound is obtained.

M.p. 141°–145° (from CH$_2$Cl$_2$-Et$_2$O-pentane);

R$_f$ (toluene:ethyl acetate 4:1): 0.18; [α]= +27°±1° (0.975% in CHCl$_3$).

The title compound may also be obtained as follows:

(b) A solution of 17 mg of 3-(S)-hydroxymethyl-4-(R)-tert.-butylsulphonyl-2-azetidinone (Example 23), 14.6 mg of imidazole and 31 mg of dimethyl-tert.butylchlorosilane in 0.4 ml of dimethylformamide is stirred for 75 minutes at room temperature, the solvent is evaporated off under a high vacuum at 25° and the residue is taken up in ethyl acetate and washed with three small portions of water. After drying the organic phase over sodium sulphate and distilling off the solvent the crystalline title compound is obtained.

Example 23:
3-(S)-hydroxymethyl-4-(R)-tert.-butylsulphonyl-2-azetidinone

A solution of 74 mg (0.2 mmol) of 1-(2,4-dimethoxybenzyl)-3-(S)-hydroxymethyl-4-(R)-tert.butylsulphonyl-2-azetidinone (see Example 20), 486 mg (1.8 mmol) of potassium peroxydisulphate and 174 mg (1.0 mmol) of dipotassium hydrogen phosphate in 4 ml of acetonitrile is stirred for 2 hours at 65° under a reflux condenser, the resulting reaction mixture is freed from acetonitrile under reduced pressure and the aqueous residue is extracted with ethyl acetate. After drying of the organic phase over Na$_2$SO$_4$ and concentration by evaporation in vacuo, a residue is obtained from which the title compound is obtained in the form of colourless crystals by adding a little methylene chloride and ether.

M.p. 196°;

R$_f$ (ethyl acetate): 0.20; [α]= +25°±1° (0.815% in CH$_3$OH).

Example 24:
N-p-methoxybenzyl-N-tert-butylthiomethylammonium chloride

A solution of 2.88 g (78.8 mmol) of hydrogen chloride in 20 ml of acetonitrile and 6.45 g (71.66 mmol) of tert.-butylmercaptan are added in succession at room temperature to a solution of 10.69 g (23.9 mmol) of 1,3,5-tris-(p-methoxybenzyl)-hexahydro-1,3,5triazine, which may be prepared analogously to the method of German Offenlegungsschrift DE-A No. 2,431,862, in 170 ml of acetonitrile. The mixture is stirred for 22 hours. Undissolved material is filtered off with suction and the filtrate is concentrated under reduced pressure. A crystalline residue is obtained which is stirred with ether and filtered off with suction.

M.p. 142°.

Example 25:
N-p-methoxybenzyl-N-tert.-butylthiomethyl (R)-glycidic acid amide The DBU salt of (R)-glycidic acid is prepared analogously to Example 5 from 845 mg (5 mmol) of 2-(S)-bromo-3-hydroxypropionic acid in 15 ml of tetrahydrofuran with 10 mmol of 1,5-diazabicyclo[5.4.0]undec-5ene. 1.03 g (5 mmol) of dicyclohexyl carbodiimide and 1.38 g (5 mmol) of N-p-methoxybenzyl-N-tert.-butylthiomethylammonium chloride are added in succession to this salt in 20 ml of methylene chloride at room temperature and the whole is stirred for 2.5 hours. The dicyclohexylurea that has precipitated is filtered off, the filtrate is diluted with methylene chloride and the whole is washed with aqueous phosphate buffer (pH 8). After drying of the organic phase over sodium sulphate and concentration by evaporation under reduced pressure, the residue is chromatographed over 70 g of silica gel using toluene/ethyl acetate (4:1). The title compound is obtained in the form of a colourless oil.

R$_f$ (toluene/ethyl acetate 1:1): 0.60;

IR (in methylene chloride): 3000–2850, 1693, 1660, 610, 1580, 1508, 1460–1450, 1415 (sh), 1364, 1242, 1210, 1180, 1110, 1037.

Example 26:
N-p-methoxybenzyl-N-tert.-butylsulphonylmethyl-(R)-glycidic acid amide 2.11 g of 90% m-chloroperbenzoic acid are added at −10° to 2.0 g of crude N-p-methoxybenzyl-N-tert.-butylthiomethyl-(R)-glycidic acid amide in 50 ml of methylene chloride. The mixture is stirred for 45 minutes and, after the addition of a further 480 mg of 90% m-chloroperbenzoic acid, the oxidation reaction is continued for 45 minutes. The m-chlorobenzoic acid that has precipitated is then filtered off with suction, the filtrate is diluted with methylene chloride and the whole is washed with 3% aqueous sodium bisulphite solution and 8% aqueous sodium bicarbonate solution. The organic phase is dried over sodium sulphate and concentrated by evaporation under reduced pressure. The residue is chromatographed over 5 g of silica gel using toluene/ethyl acetate (4:1) and the title compound is obtained in the form of a viscous, colourless oil.

R$_f$ (toluene: ethyl acetate 1:1): 0.40;

IR (in methylene chloride): 3000–2850, 1675, 1610, 1580, 1512, 1460, 1438, 1397, 1363, 1302, 1240, 1180, 1120, 1038.

Example 27:
1-p-methoxybenzyl-3-(S)-hydroxymethyl-4-(R)-tert.-butylsulphonyl-2-azetidinone Analogously to Example 8b, from 1.71 g (5 mmol) of N-p-methoxybenzyl-N-tert.-butylsulphonylmethyl-(R)-glycidic acid amide in THF, by reaction with dehydrated tetra-n-butylammonium fluoride in the presence of activated molecular sieve, there is obtained the title compound in the form of a crude product which is chromatographed over silica gel using toluene/ethyl acetate (4:1) and (2:1). The pure title compound is obtained.

M.p. 121°–122° (from methylene chloride/ether); $[\alpha]=4°\pm1°$ (0.104% in chloroform).

Example 28:
3-(S)-hydroxymethyl-4-(R)-tert.-butylsulphonyl-2-azetidinone

A solution of 68.3 mg (0.2 mmol) of 1-p-methoxybenzyl-3-(S)-hydroxymethyl-4-(R)-tert.-butylsulphonyl-2-azetidinone in 4 ml of acetonitrile is added to a solution of 428 mg (1.8 mmol) of sodium peroxydisulphate, 174 mg (1 mmol) of dipotassium hydrogen phosphate, 1 mg of iron(II) sulphate heptahydrate and 2 mg of copper-(II) acetate hydrate in 4 ml of water. The mixture is stirred for 2 hours under an argon atmosphere at a bath temperature of 65°. The resulting mixture is then concentrated to half its volume under reduced pressure and extracted with ethyl acetate. The extract is triturated with methylene chloride and ether and the pure title compound is obtained.

Example 29:
p-methoxybenzyl-3-(S)-dimethyl-tert.-butylsilyloxymethyl-4-(R)-tert.-butylsulphonyl-2-azetidinone 5.46 mmol of 1-p-methoxybenzyl-3-(S)-hydroxymethyl-4-(R)-tert.-butylsulphonyl-2-azetidinone in the form of the crude product is stirred for 90 minutes at room temperature in 20 ml of dimethylformamide with 1.65 g (2 equivalents) of dimethyl-tert.-butylchlorosilane and 0.74 g of imidazole. The solvent is distilled off under a high vacuum and the residue, dissolved in ethyl acetate, is washed with aqueous sodium bicarbonate solution. After concentration by evaporation under reduced pressure of the organic phase dried over sodium sulphate and chromatography of the crude product over 60 g of silica gel using toluene/ethyl acetate (4:1), the pure title compound is obtained.

M.p. 104°–105°;
$R_f$ (hexane:ethyl acetate 1:3): 0.78; $[\alpha]=+20°\pm1°$;

$^1$H-NMR spectrum: $\delta=4.69$ for proton (a) at the 4-(R)-carbon atom and $\delta=3.70$ for proton (b) at the 3-(S)-carbon atom (trans-compound), J a-b: approximately 2.

Example 30:
N-p-methoxybenzyl-N-tert.-butylthiomethyl-2-(S)-bromo-3-hydroxypropionic acid amide 4.13 g (20 mmol) of dicyclohexyl carbodiimide and 2.79 ml (20 mmol) of triethylamine are added at room temperature while stirring to a mixture of 3.38 g (20 mmol) of 2-(S)-bromo-3-hydroxypropionic acid and 5.151 g (20 mmol) of p-methoxybenzyl-tert.-butylthiomethylammonium chloride (Example 24) in 100 ml of tetrahydrofuran. The mixture is stirred for two hours at room temperature and the dicyclohexylurea that has precipitated is filtered off with suction. The filtrate is concentrated by evaporation under reduced pressure and the residue is chromatographed over 500 g of silica gel using toluene/ethyl acetate (9:1). The title compound is obtained in the form of a colourless, viscous oil.

$R_f$ (toluene:ethyl acetate 1:1): 0.43;
IR (in methylene chloride): 3550–3250, 2970–2850, 1640, 1610, 1580, 1508, 1460–1430, 1410 (sh), 1362, 1241, 1175, 1148, 1109, 1034.

The $^1$H-NMR spectrum indicates the existence of two rotamers.

Example 31:
N-p-methoxybenzyl-N-tert.-butylsulphonylmethyl-2-(S)-bromo-3-hydroxypropionic acid amide 4.21 g (22 mmol) of 90% m-chloroperbenzoic acid are added in portions at $-10°$ to a solution of 3.90 g (10 mmol) of N-p-methoxybenzyl-N-tert.-butylthiomethyl-2-(S)-bromo-3-hydroxypropionic acid amide in 100 ml of methylene chloride and stirring is carried out for 75 minutes at 0°. The reaction mixture is diluted with 100 ml of methylene chloride and washed with 100 ml of 3% aqueous sodium bisulphite solution and 100 ml of 8% aqueous sodium bicarbonate solution and the aqueous portions are subsequently extracted with methylene chloride. After drying of the organic phase over sodium sulphate and concentration by evaporation under reduced pressure, the crude product is obtained. Chromatography over 200 g of silica gel using toluene/ethyl acetate (4:1) yields the title compound in the form of a colourless, viscous oil.

$R_f$ (toluene:ethyl acetate 1:1): 0.36; $[\alpha]=+93°\pm1°$ (1.02% in chloroform); the $^1$H-NMR spectrum indicates the existence of two rotamers.

Example 32:
1-p-methoxybenzyl-3-(S)-hydroxymethyl-4-(R)-tert.-butylsulphonyl-2-azetidinone A solution of dehydrated tetra-n-butylammonium fluoride in tetrahydrofuran, which is prepared from tetra-n-butylammonium fluoride trihydrate by drying at 55°–60°/0.1 mm and dissolving in 40 ml of tetrahydrofuran, is added dropwise at 0° to a solution of 1.426 g (3.38 mmol) of N-p-methoxybenzyl-N-tert.-butylsulphonylmethyl-2-(S)-bromo-3-hydroxypropionic acid amide in 6 ml of tetrahydrofuran. Activated molecular sieve (4 Å) is added to the reaction mixture and the whole is stirred for 2 hours at 0°. The molecular sieve is filtered off and washed with methylene chloride; 600 ml of ether and 75 ml of buffer solution having a pH of 8 are added to the combined filtrates. After drying over sodium sulphate and concentration by evaporation in vacuo, the crude product is obtained which is purified by chromatography over 50 g of silica gel using toluene:ethyl acetate (4:1) and (2:1).

Example 33:
N-p-methoxybenzyl-N-tert.-butylthiomethyl-2-(S)-bromo-3-(R)-hydroxybutyramide In succession, 2.76 g (10 mmol) of p-methoxybenzyl-tert.-butylthiomethylammonium chloride (Example 24), 2.06 g (10 mmol) of dicyclohexyl carbodiimide and, dropwise, 1.40 ml (10 mmol) of triethylamine are added at room temperature to a solution of 1.83 g (10 mmol) of 2-(S)-bromo-3-(R)-hydroxybutyric acid prepared analogously to a method of Shimohigashi Y. et al., Bull. Chem. Soc. Japan 52, 949 (1979). The resulting reaction mixture is stirred at room temperature for 2 hours. The dicyclohexylurea that has precipitated is filtered off with suction and the filtrate is diluted with methylene chloride and washed with water and phosphate buffer solution having a pH of 8. The organic phase is dried over sodium sulphate and concentrated by evaporation and the oily residue is chromatographed over silica gel using toluene/ethyl acetate. The title compound is obtained in the form of a colourless, viscous oil.

$R_f$ (toluene/ethyl acetate 1:1): 0.55;

IR (in methylene chloride): 3550–3200, 2950–2850, 1632, 1608, 1508, 1457, 1438, 1407, 1360, 1242, 1202, 1175, 1150, 1028.

Example 34:
N-p-methoxybenzyl-N-tert.-butylsulphonylmethyl-2-(S)-bromo-3-(R)-hydroxybutyramide 2.06 g (approximately 2.2 equivalents) of 90% m-chloroperbenzoic acid are added at −14°, while stirring, to a solution of 1.97 g (4.89 mmol) of N-p-methoxybenzyl-N-tert.-butylthiomethyl-2-(S)-bromo-3-(R)-hydroxybutyramide in 50 ml of methylene chloride. The reaction mixture is stirred at 0° for 80 minutes. The m-chloroperbenzoic acid that has precipitated is filtered off and the filtrate is diluted with methylene chloride and shaken in succession with 3% aqueous sodium bisulphite solution and 8% aqueous sodium bicarbonate solution. The organic phase is dried over sodium sulphate and concentrated by evaporation under reduced pressure and the residue is chromatographed over silica gel using toluene/ethyl acetate (7:1) and (6:1). The title compound is obtained in the form of a colourless viscous oil.

$R_f$ (toluene/ethyl acetate 1:1): 0.43; $[\alpha] = +88° \pm 1°$ (1.01% in chloroform). The $^1$H-NMR spectrum (400 MHz in CDCl$_3$) indicates the existence of two rotamers in the ratio of 1.3:1.

Example 35:
N-p-methoxybenzyl-N-tert.-butylthiomethyl-(2R,3R)-2,3-epoxybutyramide A solution of 1.83 g (10 mmol) of 2-(S)-bromo-3-(R)-hydroxybutyric acid and 3.045 g (20 mmol) of 1,5-diazabicyclo[5.4.0]undec-5-ene in 30 ml of tetrahydrofuran is stirred at room temperature for one hour and concentrated under reduced pressure. The residue is dissolved in 40 ml of methylene chloride. After adding 2.06 g (10 mmol) of dicyclohexyl carbodiimide and 2.76 g (10 mmol) of p-methoxybenzyl-tert.-butylthiomethylammonium chloride, the whole is stirred at room temperature for 2.5 hours. The dicyclohexylurea that has formed is filtered off and the filtrate is diluted with methylene chloride and washed with aqueous phosphate buffer solution having a pH of 8. The organic phase is dried over sodium sulphate and concentrated by evaporation in vacuo and the residue is chromatographed over silica gel using toluene/ethyl acetate (9:1). The title compound is obtained in the form of a colourless, viscous oil.

$R_f$ (toluene/ethyl acetate 1:1): 0.40.

IR (in methylene chloride): 3050–2850, 1690, 1660, 1640 (sh), 1607, 1506, 1460–1438, 1400 (sh), 1362, 1240, 1204, 1175, 1150, 1133, 1108, 1035.

Example 36:
N-p-methoxybenzyl-N-tert.-butylsulphonylmethyl-(2R,3R)-2,3-epoxybutyramide (a) 340 ml of 1,5-diazabicyclo[5.4.0]undec-5-ene in 1 ml of tetrahydrofuran are added at −14° and with the exclusion of moisture to a solution of 486 mg (1.1 mmol) of N-p-methoxybenzyl-N-tert.-butylsulphonyl methyl-2-(S)-bromo-3-(R)-hydroxybutyramide (Example 34) in 8 ml of tetrahydrofuran. The solution is stirred at room temperature for 75 minutes. After adding methylene chloride, the organic phase is extracted by shaking with 15% aqueous citric acid solution and 8% aqueous sodium bicarbonate solution. The organic phase is dried over sodium sulphate and concentrated by evaporation under reduced pressure. After chromatography of the residue over silica gel using toluene/ethyl acetate (4:1) the title compound is obtained in the form of a colourless viscous oil.

$R_f$ (toluene/ethyl acetate 1:1): 0.29; $[\alpha] = +45° \pm 1°$ (1.065% in CHCl$_3$). The $^1$H-NMR spectrum (400 MHz in CDCl$_3$) indicates the existence of two rotamers in the ratio of 1:2.8.

(b) 1.80 g (5.57 mmol) of N-p-methoxybenzyl-N-tert.-butylthiomethyl-(2R,3R)-2,3-epoxybutyramide in 50 ml of methylene chloride are stirred at 0° for 90 minutes with 2.35 g (approximately 12.25 mmol) of m-chloroperbenzoic acid. The m-chloroperbenzoic acid that has precipitated is filtered off and the filtrate is diluted with methylene chloride and extracted by shaking in succession with 3% aqueous sodium bisulphite solution and 8% aqueous sodium bicarbonate solution. The organic phase is dried over sodium sulphate and concentrated by evaporation under reduced pressure and the residue is chromatographed over silica gel using toluene/ethyl acetate (9:1) and (4:1). The title compound is obtained.

Example 37:
1-p-methoxybenzyl-3-(S)-(1'-(R)-hydroxyethyl)-4-(R)-tert.-butylsulphonyl-2-azetidinone (a) 7 ml of a solution of dehydrated tetra-n-butylammonium fluoride in THF, prepared by dehydrating 5 g of tetra-n-butylammonium fluoride trihydrate at 55° and 0.1 torr and making up to 20 ml with tetrahydrofuran, are added at 0°, while stirring and with the exclusion of moisture, to a solution of 398 mg (1.12 mmol) of N-p-methoxybenzyl-N-tert.-butylsulphonylmethyl-(2R,3R)-2,3-epoxybutyramide in 2.5 ml of tetrahydrofuran. Activated molecular sieve of 4 Å is added to the reaction mixture and the whole is stirred for 2 hours. The molecular sieve is filtered off with suction and washed four times with 20 ml of methylene chloride each time. 5 parts of diethyl ether are added separately to each filtrate and each filtrate is washed in succession with aqueous phosphate buffer solution having a pH of 8. The combined organic phases are dried over magnesium sulphate and concentrated by evaporation under reduced pressure. The residue is chromatographed over 20 g of silica gel using toluene/ethyl acetate (3:1) and the crystalline title compound is obtained.

M.p. 112°–113° (Kofler, from methylene chloride, diethyl ether, pentane);

$R_f$ (toluene/ethyl acetate 1:1): 0.27; $[\alpha] = +9° \pm 1°$ (1.105% in chloroform);

$^1$H-NMR spectrum (400 MHz in CDCl$_3$): $\delta = 4.65$ for proton (a) at the 4-(R)-carbon atom, $\delta = 3.61$ for proton (b) at the 3-(S)-carbon atom and $\delta = 4.09$ for proton (c)

at the 1'-(R)-carbon atom of the hydroxyethyl group; J a-b: approximately 2, J b-c: approximately 7.

(b) The title compound is obtained analogously to Example 37(a), from 803 mg (1.84 mmol) of N-p-methoxybenzyl-N-tert.-butylsulphonylmethyl-2-(S)-bromo-3-(R)-hydroxybutyramide (Example 34) in 5 ml of tetrahydrofuran, by adding dehydrated tetrabutylammonium fluoride in tetrahydrofuran in the presence of activated molecular sieve, after two hours' reaction time at 0° and working up.

Example 38:
3-(S)-(1'-(R)-hydroxyethyl)-4-(R)-tert.-butylsulphonyl-2-azetidinone (a) A solution of 71 mg (0.2 mmol) of 1-p-methoxybenzyl-3-(S)-(1'-(R)-hydroxyethyl)-4-(R)-tert.-butylsulphonyl-2-azetidinone in 4 ml of acetonitrile is added to a well-stirred solution, heated to 65°, of 428 mg (1.8 mmol) of sodium peroxydisulphate, 174 mg (1 mmol) of dipotassium hydrogen phosphate, 1 mg of iron(II) sulphate heptahydrate and 2 mg of copper(II) acetate hydrate in 4 ml of water. The reaction mixture is stirred for 2 hours at 65°. The organic solvent is distilled off under reduced pressure and the aqueous residue is extracted with ethyl acetate. After concentrating the organic phase in vacuo, the residue is crystallised from methylene chloride/diethyl ether and the title compound is obtained.

M.p. 194°; $R_f$(ethyl acetate): $[\alpha] = +13 \pm 1°$ (0.75% in methanol);

$^1$H-NMR spectrum (400 MHz in CD$_3$OD): $\delta = 5.04$ for proton (a) at the 4-(R)-carbon atom, $\delta = 3.58$ for proton (b) at the 3-(S)-carbon atom and $\delta = 4.18$ for proton (c) at the 1'-(R)-carbon atom of the hydroxyethyl group; J a-b: approximately 2, J b-c: approximately 4.5.

(b) A solution of 4.172 g (7.6 mmol) of cerium(IV) ammonium nitrate in 10 ml of water is added dropwise, while stirring at 0°, to a solution of 710 mg (2 mmol) of 1-p-methoxybenzyl-3-(S)-(1'-(R)-hydroxyethyl)-4-(R)-butylsulphonyl-2-azetidinone in 20 ml of acetonitrile and the mixture is stirred at room temperature for one hour. The mixture is diluted with 50 ml of ethyl acetate and the aqueous layer, separated off, is extracted twice with 50 ml of ethyl acetate in each case. The combined organic phases are dried over sodium sulphate and concentrated by evaporation under reduced pressure. A small amount of methanol is added to the residue and the whole is stirred with diethyl ether so that the p-methoxybenzaldehyde resulting from oxidation is dissolved and the title compound is obtained in the form of white crystals which are subsequently filtered off with suction and washed with diethyl ether; the compound is identical to the compound obtained according to Example 38(a).

Example 39:
3-(S)-(1'-(R)-tert.-butyldimethylsilyloxyethyl)-4-(R)-tert.-butylsulphonyl-2-azetidinone 135 mg (0.574 mmol) of 3-(S)-(1'-(R)-hydroxyethyl)-(R)-tert.-butylsulphonyl-2-azetidinone are stirred for two hours at room temperature with 173 mg (1.15 mmol) of tert.-butyldimethylchlorosilane and 78 mg (1.15 mmol) of imidazole in 3 ml of dimethylformamide. The reaction mixture is concentrated by evaporation in vacuo. The residue is taken up in ethyl acetate and washed with 8% aqueous sodium bicarbonate solution. After drying of the organic phase over sodium sulphate and concentration by evaporation under reduced pressure, the title compound is obtained in the form of a crystalline residue. This residue is freed from traces of imidazole by chromatography over silica gel using toluene/ethyl acetate (4:1) and white crystals are obtained.

M.p. 196°; $R_f$ (toluene/ethyl acetate 1:1): 0.48; $[\alpha] = +11° \pm 1°$.

Example 40:
1-p-methoxybenzyl-3-(S)-(1'-(R)-trichloroethoxycarbonyloxyethyl)-4-(R)-tert.-butylsulphonyl-2-azetidinone A solution of 1.777 g (5 mmol) of 1-p-methoxybenzyl-3-(S)-(1'-(R)-hydroxyethyl)-4-(R)-tert.-butylsulphonyl-2-azetidinone (Example 37), 0.9 ml (6.5 mmol) of triethylamine, 0.883 ml (6.5 mmol) of chloroformic acid 2,2,2-trichloroethyl ester and 643 mg (5.25 mmol) of 4-dimethylaminopyridine in 25 ml of methylene chloride is stirred for 16 hours at 5°, subsequently diluted with 100 ml of methylene chloride and washed with 50 ml of 5% aqueous citric acid solution and 50 ml of 8% aqueous sodium bicarbonate solution. The aqueous phase is extracted with methylene chloride and the combined organic extracts are dried over sodium sulphate and concentrated by evaporation in vacuo. The crude product is chromatographed over 100 g of Merck silica gel using toluene/ethyl acetate (9:1) and the title compound is obtained in the form of colourless crystals.

M.p. 142°–144°; $R_f$(toluene/ethyl acetate 4:1): 0.49; $[\alpha] = +36° \pm 1°$ (0.958% in chloroform).

Example 41:
3-(S)-(1'-(R)-trichloroethoxycarbonyloxyethyl-4-(R)-tert.-butylsulphonyl-2-azetidinone A solution of 1.062 g (2 mmol) of 1-p-methoxybenzyl-3-(S)-(1'-(R)-trichloroethoxycarbonyloxyethyl)-4-(R)-tert.-butylsulphonyl-2-azetidinone in 20 ml of acetonitrile is stirred at 5° with a solution of 4.17 g (7.6 mmol) of cerium(IV) ammonium nitrate in 10 ml of water for one hour at room temperature. The mixture is extracted twice with 75 ml of ethyl acetate and the organic phases are washed with 75 ml of 8% aqueous sodium bicarbonate solution, dried over sodium sulphate and concentrated by evaporation under reduced pressure. The crude product is chromatographed over 50 g of Merck silica gel using toluene/ethyl acetate (4:1) and the title compound is obtained in crystalline form.

M.p. 165°–166°; $R_f$ (toluene/ethyl acetate 1:1): 0.52; $[\alpha] = +38° \pm 1°$ (1.499% in chloroform).

Example 42:
1-p-methoxybenzyl-3-(S)-(1'-(R)-allyloxycarbonyloxyethyl)-4-(R)-tert.-butylsulphonyl-2-azetidinone 0.68 g (2 mmol) of tetra-n-butylammonium bisulphate is added to a two-phase system comprising a solution of 1.77 g (5 mmol) of 1-p-methoxybenzyl-3-(S)-(1'-(R)-hydroxyethyl)-4-(R)-tert.-butylsulphonyl2-azetidinone (Example 37) in 20 ml of methylene chloride and 20 ml of a 1N aqueous sodium hydroxide solution. 0.8 ml (7.5 mmol) of chloroformic acid allyl ester is added at 0° with vigorous stirring. After 20 minutes and after 40 minutes, a further 0.8 ml of chloroformic acid allyl ester is added. After 60 minutes' reaction time, methylene chloride is added to the mixture, the aqueous phase is separated off and the organic phase is washed in succession with 5% aqueous citric acid solution and 8% aqueous sodium bicarbonate solution. After drying of the organic phase over sodium sulphate and concentration by evaporation under reduced pressure, the crude product is obtained as residue and is purified by chromatography over Merck silica gel using toluene/ethyl acetate (9:1).

M.p. 90°–91°; $R_f$ (toluene/ethyl acetate 4:1): 0.43; $[\alpha] = +46° \pm 1°$ (1.49% in chloroform).

Example 43:
3-(S)-(1'-(R)-allyloxycarbonyloxyethyl)-4-(R)-tert.-butylsulphonyl-2-azetidinone A solution of 2.46 g (4.48 mmol) of cerium(IV) ammonium nitrate in 6 ml of water is added at 0° to a solution of 518 mg (1.18 mmol) of 1-p-methoxybenzyl-3-(S)-(1'-(R)-allyloxycarbonyloxyethyl)-4-(R)-tert.-butylsulphonyl-2-azetidinone in 12 ml of acetonitrile and the whole is stirred for one hour at room temperature. After extraction with ethyl acetate, drying of the organic phase over sodium sulphate and concentration by evaporation under reduced pressure, the crude product is obtained which is purified by chromatography over 20 g of Merck silica gel using toluene/ethyl acetate (4:1 and 1:1).

M.p. 137°–138°; $[\alpha] = +49° \pm 1°$ (1.067% in chloroform);

$R_f$ (toluene/ethyl acetate 1:1): 0.48.

Example 44: (2S,3R)-2-bromo-3-hydroxybutyric acid p-methoxybenzylamide

In the course of 20 minutes, 4.16 g of 1-hydroxybenztriazole and 5.63 g of dicyclohexyl carbodiimide in 60 ml of THF are added dropwise to a solution, stirred at room temperature under an argon atmosphere, of 5 g of (2S,3R)-2-bromo-3-hydroxybutyric acid and 3.52 g of p-methoxybenzylamine in 60 ml of absolute THF. The reaction mixture is stirred for 48 hours, the dicyclohexylurea that has formed is filtered off and washed several times with THF and the filtrate is concentrated by evaporation. The resulting crude product contains dicyclohexylurea and hydroxybenztriazole as impurities. After chromatography of the mixture over silica gel (system: toluene; toluene/ethyl acetate - 1:4) and crystallisation of the pure fractions from methylene chloride/ether, the title compound is obtained having a melting point of 122°–124°. $[\alpha] = -7° \pm 1°$ (1.112% in chloroform).

Example 45:
(2S,3R)-2-bromo-3-tert.-butyldimethylsilyloxybutyric acid p-methoxybenzylamide 4.875 g of tert.-butyldimethylchlorosilane and 3.315 g of imidazole are added to a solution of 7.8 g of (2S,3R)-2-bromo-3-hydroxybutyric acid pmethoxybenzylamide in 300 ml of dimethylformamide and the whole is stirred for 24 hours at room temperature. The reaction mixture is then concentrated under a high vacuum to form a syrup and, after the addition of ice-cold saturated NaHCO₃ solution, is extracted twice by shaking with chloroform. The organic extracts are washed at 0° in succession with NaHCO₃ solution, 1% citric acid, NaHCO₃ solution and water, dried and concentrated by evaporation. Crystallisation from methylene chloride/ether/petroleum ether of the crude product so obtained yields the pure title compound.

M.p. 112°–114°; $[\alpha] = -23° \pm 1°$ (1.54% in chloroform);

Example 46:
(2S,3R)-2-bromo-3-tert.-butyldimethylsilyloxybutyric acid
N-tert.-butoxycarbonylmethyl-N-p-methoxybenzylamide A solution of 4.17 g of (2S,3R)-2-bromo-2-tert.-butyldimethylsilyloxybutyric acid p-methoxybenzylamide in 10 ml of THF is added dropwise to a mixture, stirred at 0° under an argon atmosphere, of 550 mg of a 55–66% dispersion of sodium hydride in oil and 1.52 g of bromoacetic acid tert.-butyl ester in 25 ml of THF. After 30 minutes' reaction time, the mixture is brought to room temperature and stirred for a further 90 minutes. The undissolved residue is filtered off from the reaction mixture, the filtration residue is washed with THF and the filtrate is concentrated by evaporation. After chromatography of the crude product over 400 g of silica gel (system: toluene; toluene/ethyl acetate - 95:5), the pure, amorphous title compound is obtained. $[\alpha] = +32° \pm 1°$ (0.4% in chloroform).

Example 47:
1-p-methoxybenzyl-3-(S)-(1'-(R)-hydroxyethyl)-4-(S)-tert.-butoxycarbonyl-2-azetidinone 12.45 g of tetrabutylammonium fluoride trihydrate are dehydrated with 30 g of molecular sieve (type 4171/16) in THF for 22 hours at room temperature. The mixture is cooled to 0°–5°, a solution of 3.0 g of (2S,3R)-2-bromo-3-tert.-butyldimethylsilyloxybutyric acid N-tert.-butoxycarbonylmethyl-N-p-methoxybenzylamide is added and the whole is stirred for 2 hours at room temperature. The molecular sieve is filtered off and washed with 80 ml of methylene chloride and the filtrate is diluted with 500 ml of ether and washed twice with phosphate buffer solution (pH 8). The organic phases are dried and concentrated by evaporation. The crude product that forms is taken up in methylene chloride and the solution is washed in succession with 1N sulphuric acid, water and NaHCO₃ solution, dried and concentrated by evaporation. After subsequent chromatography over silica gel and crystallisation of the uniform fractions from methylene chloride/ether/petroleum ether, the pure title compound is obtained having a melting point of 85°–87°; $[\alpha] = +13° \pm 1°$ (1.20% in chloroform)

Example 48:
1-p-methoxybenzyl-3-(S)-(1'-(R)-trichloroethoxycarbonyloxyethyl)-4-(S)-tert.-butoxycarboyl-2-azetidinone 500 mg of 1-p-methoxybenzyl-3-(S)-(1'-(R)-hydroxyethyl)-4-(R)-tert.-butoxycarbonyl-2-azetidinone are dissolved in 7.5 ml of methylene chloride. While stirring and under an argon atmosphere, there are added to the solution, cooled to 0°, 0.27 ml of triethylamine, 0.27 ml of chloroformic acid 2,2,2-trichloroethyl ester and 195 mg of dimethylaminopyridine, stirring is continued for a further hour at 0° and the mixture is left to stand for 18 hours at 5°. The mixture is then poured into ice-water and diluted with methylene chloride and the organic phase is washed in succession with 5% citric acid and NaHCO₃ solution, dried and concentrated by evaporation under a water-jet vacuum. After chromatography over silica gel (system: toluene; toluene/ethyl acetate 95:5 and 90:10) and recrystallisation of the uniform fractions from methylene chloride/ether/petroleum ether, the title compound is obtained.

M.p. 102°–104°; $[\alpha] = +65° \pm 1°$ (1.29% in chloroform).

Example 49:
3-(S)-(1'-(R)-trichloroethoxycarbonyloxyethyl)-4-(S)-tert.-butoxycarbonyl-2-azetidinone A solution, cooled to −10°, of 510 mg of 1-p-methoxybenzyl-3-(S)-(1'-(R)-trichloroethoxycarbonyloxyethyl)-4-(S)-tert.-butoxycarbonyl-2-azetidinone in 10 ml of acetonitrile is stirred for 15 minutes, 2.25 g of cerium(IV) ammonium nitrate in 6.25 ml of water are added and stirring is continued for 30 minutes. The reaction mixture is poured into ice-water and extracted with ethyl acetate. The organic phases are washed with saturated, aqueous NaHCO$_3$ solution, dried and concentrated by evaporation. After chromatography of the crude product over 50 g of silica gel and subsequent crystallisation of the pure fractions from methylene chloride/ether/petroleum ether, 285 mg of pure title compound are obtained.

M.p. 138°–140°; $[\alpha] = +29° \pm 1°$ (0.917% in chloroform).

Example 50:
3-(S)-(1'-(R)-trichloroethoxycarbonyloxyethyl)-4-(S)-carboxylic acid 2-azetidinone 282 mg of 3-(S)-(1'-(R)-trichloroethoxycarbonyloxyethyl)-4-(S)-tert.-butoxycarbonyl-2-azetidinone are dissolved at 0° in 10 ml of trifluoroacetic acid. After reaction for 1 hour at room temperature, the reaction mixture is concentrated by evaporation under a high vacuum and the resulting title compound is further processed without being purified;

$[\alpha] = +25° \pm 1°$ (0.834% in chloroform).

Example 51:
3-(R)-(1'-(R)-trichloroethoxycarbonyloxyethyl)-4-(R)-acetoxy-2-azetidinone 271 mg of lead(IV) acetate (approximately 10% acetic acid content) are added to a solution, stirred under an argon atmosphere at room temperature, of 241 mg of 3-(S)-(1'-(R)-trichloroethoxycarbonyloxyethyl)-4-(S)-carboxylic acid 2-azetidinone in a mixture of 7 ml of THF and 1.2 ml of dimethylformamide and stirring is carried out until reaction of the substrate is complete (approximately 1 hour). Excess oxidising agent is destroyed by adding 0.1 ml of ethylene glycol (10 minutes/room temperature). The lead(II) acetate that has formed is filtered off from the reaction mixture, the filtration residue is rinsed with THF and the filtrate is concentrated by evaporation. The resulting oily residue is taken up in methylene chloride, washed in succession twice in each case with saturated aqueous NaHCO$_3$ solution, water and saturated NaCl solution, dried and concentrated by evaporation. Chromatography of the residue over silica gel (system: toluene; toluene/ethyl acetate - 80:20) yields the pure title compound.

$[\alpha] = +28° \pm 1°$ (1.3% in chloroform).

Example 52: (2R,3R)-2,3-epoxybutyric acid p-methoxybenzylamide 50 ml of 50% NaOH solution and 456 mg (2 mmol) of benzyltriethylammonium chloride are added to a solution of 6.04 g (20 mmol) of (2R,3R)-2-bromo-3-hydroxybutyric acid p-methoxybenzylamide in 150 ml of methylene chloride. The two phase mixture is vigorously stirred for 20 hours at room temperature. The organic layer is separated off and the aqueous phase is subsequently extracted with methylene chloride. The combined methylene chloride solutions are dried and concentrated by evaporation. The crude product that forms is chromatographed over 40 times the amount by weight of silica gel in a methylene chloride/methanol - 99:1 system. After crystallisation of the pure fractions from methylene chloride/ether/petroleum ether, the title compound is obtained, melting point 75°–76°.

Example 53: (2R,3R)-2,3-epoxybutyric acid N-tert.-butoxycarbonylmethy)-N-p-methyl-N-p-methoxybenzylamide A solution of 2.21 g of (2R,3R)-2,3-epoxybutyric acid p-methoxybenzylamide in 100 ml of THF is added dropwise to a mixture, stirred at 0° under an argon atmosphere, of 550 mg of a sodium hydride dispersion (55–60% in oil) and 1.52 ml of bromoacetic acid tert.-butyl ester in 25 ml of THF. The reaction mixture is heated to room temperature and stirred for a further hour (the course of the reaction is monitored by thin-layer chromatography). Total reaction time: 90 minutes. The insoluble portions are filtered off and washed with THF and the combined filtrates are concentrated by evaporation. The crude product that forms is purified by chromatography over 150 g of silica gel (system: toluene, toluene/ethyl acetate -80:20). Concentration by evaporation of the pure fractions yields the amorphous title compound. IR spectrum: bands, inter alia, at 1740, 1670, 1650, 1615, 1517, 1465, 1360 and 1035.

Example 54:
1-p-methoxybenzyl-3-(S)-(1'-(R)-hydroxyethyl)-4-(S)-tert.-butoxycarbonyl-2-azetidinone 9.23 g of tetrabutylammonium fluoride trihydrate are left to stand for 16 hours at 5° with 40 g of molecular sieve (type 4171/16, pre-dried at 300°) in 80 ml of THF. The mixture is cooled to 0°, a solution of 2.8 g of (2R,3R)-2,3-epoxybutyric acid N-tert.-butoxycarbonylmethyl-N-methoxybenzylamide in 20 ml of THF is added and the whole is stirred for 2 hours at 0°–5°. The molecular sieve is filtered off by subsequently washing with THF and the filtrate is introduced directly onto a column, prepared in toluene, containing 250 g of silica gel. The fractions, which have been concentrated by evaporation and eluted with a 70:30 mixture of toluene-/ethyl acetate, are taken up in methylene chloride, washed in succession twice with 1N sulphuric acid, with saturated aqueous NaHCO$_3$ solution and with water, dried and concentrated by evaporation. After brief chromatography over silica gel (toluene, toluene-/ethyl acetate - 60:40) and crystallisation from methylene chloride/ether/petroleum ether, the pure title compound is obtained, having a melting point of 85°–87°. (Identical with the product obtained according to the details in Example 47).

Example 55:
1-p-methoxybenzyl-3-(S)-(1'-(R)-trichloroethoxycarbonyloxyethyl)-4-(S)-carboxylic acid 2-azetidinone 350 mg of 1-p-methoxybenzyl-3-(S)-1'-(R)-trichloroethoxycarbonyloxyethyl)-4-(S)-tert.- butoxycarbonyl-2-azetidinone are dissolved at 0° in 10 ml of trifluoroacetic acid. After reaction for one hour at room temperature, the reaction mixture is concentrated by evaporation under a high vacuum and the resulting title compound, which does not contain any starting material, is further processed without being purified.

IR spectrum: bands, inter alia, at 1768, 1722, 1611, 1584, 1515 and 1035.

Example 56:
1-p-methoxybenzyl-3-(R)-(1'-(R)-trichloroethoxycarbonyloxyethyl)-4-(R)-acetoxy-2-azetidinone 360 mg of lead(IV) acetate (approximately 10% acetic acid content) are added to a solution, stirred at room temperature under an argon atmosphere, of 320 mg of 1-p-methoxybenzyl-3-(S)-(1'-(R)-trichloroethoxycarbonyloxyethyl)-4-(S)-carboxylic acid 2-azetidinone in a mixture of 10 ml of THF and 1.5 ml of dimethylformamide and stirring is carried out until reaction of the substrate is complete (approximately 1 hour). Excess oxidising agent is destroyed by adding 0.1 ml of ethylene glycol (10 minutes/room temperature). The lead(II) acetate that has formed is filtered off from the reaction mixture, the filtration residue is rinsed with THF and the filtrate is concentrated by evaporation. The resulting oily residue is taken up in methylene chloride, washed in succession twice in each case with saturated aqueous $NaHCO_3$ solution, water and saturated NaCl solution, dried and concentrated by evaporation. Chromatography of the residue over 50 g of silica gel (system: toluene; toluene/ethyl acetate - 90:10) yields the pure title compound.

IR spectrum: bands, inter alia, at 1780, 1765 (sh), 1615, 1590, 1517, 1180 and 1035.

Example 57:
3-(R)-(1'-trichloroethoxycarbonyloxyethyl)-4-(R)acetoxy-2-azetidinone A solution, cooled to -10°, of 510 mg of 1-p-methoxybenzyl-3-(R)-(1'-(R)-trichloroethoxycarbonyloxyethyl)-4-(R)-acetoxy-2-azetidinone in 11 ml of acetonitrile is stirred for 15 minutes, 2.40 g of cerium(IV) ammonium nitrate in 5.5 ml of water are added and stirring is continued for 2 hours. The reaction mixture is poured into ice-water and extracted with ethyl acetate. The organic phases are washed with saturated, aqueous $NaHCO_3$ solution, dried and concentrated by evaporation. After chromatography of the crude product over 50 g of silica gel (toluene, toluene/ethyl acetate - 90:10), the pure amorphous title compound is obtained.

$[\alpha] = +27° \pm 1°$ (0.9% in chloroform).

Example 58:
1-p-methoxybenzyl-3-(S)-(1'-(R)-allyloxycarbonyloxyethyl)-4-(S)-tert.-butoxycarbonyl-2-azetidinone 24 ml of 1N NaOH, 820 mg of tetrabutylammonium bisulphate and 1 ml of chloroformic acid allyl ester are added at 0° to a solution of 2 g of 1-p-methoxybenzyl-3-(S)-(1'-(R)-hydroxyethyl)-4-(S)-tert.-butoxycarbonyl-2-azetidinone in 24 ml of methylene chloride and the whole is stirred vigorously. After 20 minutes' and 40 minutes' reaction time, further portions (1 ml in each case) of chloroformic acid allyl ester are added. The reaction mixture is diluted with methylene chloride, the aqueous phase is separated off and the organic layer is washed in succession with 5% aqueous citric acid and 8% aqueous $NaHCO_3$ solution, dried and concentrated by evaporation. After purification by chromatagraphy, the pure amorphous title compound is obtained.

IR spectrum: bands, inter alia, at 1765, 1745 (sh), 1615, 1593, 1515, 1160 and 1035.

Example 59:
1-p-methoxybenzyl-3-(S)-(1'-(R)-allyloxycarbonyloxyethyl)-4-(S)-carboxylic acid 2-azetidinone 1.6 g of 3-(1-p-methoxybenzyl)-3-(S)-(1'-(R)-allyloxycarbonyloxyethyl)-4-(S)-tert.-butoxycarbonyl-2-azetidinone are dissolved at 0° in 10 ml of trifluoroacetic acid. After reaction for one hour at room temperature, the reaction mixture is concentrated by evaporation under a high vacuum and the resulting title compound is further processed without being purified.

$[\alpha] = +85° \pm 1°$ (1.0% in chloroform).

Example 60:
1-p-methoxybenzyl-3-(R)-(1'-(R)-allyloxycarbonyloxyethyl)-4-(R)-acetoxy-2-azetidinone 1.6 g of lead(IV) acetate (approximately 10% acetic acid content) are added to a solution, stirred at room temperature under an argon atmosphere, of 1.4 g of 1-p-methoxybenzyl-3-(S)-(1'-(R)-allyloxycarbonyloxyethyl)-4-(S)-carboxylic acid 2-azetidinone in a mixture of 45 ml of THF and 6.6 ml of dimethylformamide and stirring is carried out for approximately 1 hour until reaction of the substrate is complete. Excess oxidising agent is destroyed by adding 0.5 ml of ethylene glycol (10 minutes/room temperature). The lead(II) acetate that has formed is filtered off from the reaction mixture, the filtration residue is rinsed with THF and the filtrate is concentrated by evaporation. The resulting oily residue is taken up in methylene chloride, washed in succession twice in each case with saturated, aqueous $NaHCO_3$ solution, water and saturated NaCl solution, dried and concentrated by evaporation. Chromatography of the residue over silica gel (toluene; toluene/ethyl acetate - 90:10) yields the pure title compound.

$[\alpha] = +90° \pm 1°$ (1.0% in chloroform).

Example 61:
3-(R)-(1'-(R)-allyloxycarbonyloxyethyl)-4-(R)-acetoxy-2-azetidinone A solution of 5.37 g of cerium(IV) ammonium nitrate in 15 ml of water is added at 10° to a solution of 900 mg (1.18 mmol) of 1-p-methoxybenzyl- 3-(R)-(1'-(R)-allyloxycarbonyloxyethyl)-4-(R)-acetoxy-2-azetidinone in 30 ml of acetonitrile and stirring is carried out for 2 hours at room temperature. After extaction with ethyl acetate, washing with saturated $NaHCO_3$ solution, drying of the organic phase over sodium sulphate and concentration by evaporation under reduced pressure, the crude title compound is obtained which is purified by chromatography over silica gel using toluene/ethyl acetate (4:1 and 1:1).

$[\alpha] = +84° \pm 1°$ (1.0% in chloroform).

We claim:

1. A process which comprises the step of treating in an aprotic organic solvent either
   (i) an oxirane carboxylic acid amide of the formula:

$$R_1CH\underset{O}{\overset{H}{\underset{\diagdown\diagup}{C}}}C-CON\diagdown_{R_4'}^{\diagup CH_2Y}$$

wherein
$R_1$ is hydrogen or lower alkyl;
Y is $-SOR_3$, $-SO_2R_3$ or $-COOR_3$ in which $R_3$ is tert.-lower alkyl, cycloalkyl-lower alkyl, triphenylmethyl, naphthyl, phenyl, or phenyl substituted with one or two members selected from the group consisting of lower alkyl, lower alkoxy, nitro and halo;

R₄' is a group capable of protecting the nitrogen atom to which it is bound against reaction with fluoride ion;

the configuration about the carbon atom of the depicted oxirane ring to which R₁ is bound when R₁ is lower alkyl is either R or S; and the configuation about the other carbon atom of the oxirane ring is R; or (ii) a 2,3-disubstituted alkanoic acid amide of the formula:

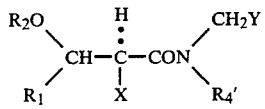

wherein

R₁, R₄', and Y are as herein defined;

R₂ is hydrogen or a protecting group capable of protecting an alcoholic hydroxy group from oxidation;

X is a nucleofugal group;

the configuration about the carbon atom to which R₁ is bound when R₁ is lower alkyl is either R or S; and the configuration about the carbon atom to which X is bound is R;

with a source of fluoride ion to yield a (3S)-3,4-trans-disubstituted azetidinone of the formula:

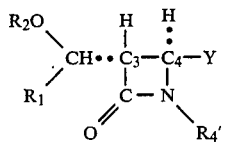

wherein R₁, R₂, R₄', and Y are as herein defined with the proviso that R₂ is hydrogen when said oxirane carboxylic acid is treated with the source of fluoride ion;

the configuration about the carbon atom designated 3 is R;

the configuration about the carbon atom designated 4 is such as to correspond to R if Y is —SOR₃ or —SO₂R₃, and to S if Y is —COOR₃; and the configuration about the carbon atom to which R₁ is bound when R₁ is lower alkyl is either R or S.

2. The process according to claim 1 wherein R₁ is hydrogen or methyl, Y is —SO₂R₃ or —COOR₃, R₃ is tert.-lower alkyl or phenyl, and R₄' is benzyl or phenyl each of which is substituted with one or two methoxy groups.

3. The process according to claim 2 wherein R₃ is tert.-butyl or phenyl and R₄' is 4-methoxybenzyl, 2,4-dimethoxybenzyl, 4-methoxyphenyl, or 3,4-dimethoxyphenyl.

4. The process according to claim 3 wherein R₁ is hydrogen, Y is tert.-butylsulfonyl and R₄' is 2,4-dimethoxybenzyl, said (3S)-3,4-trans-disubstituted azetidinone thereby yielded being 1-(2,4-dimethoxybenzyl)-3-(S)-hydroxymethyl-4-(R)-tert.-butylsulfonyl-2-azetidinone.

5. The process according to claim 3 wherein R₁ is hydrogen, Y is tert.-butylsulfonyl and R₄' is 4-methoxybenzyl, said (3S)-3,4-trans-disubstituted azetidinone thereby yielded being 1-(4-methoxybenzyl)-3-(S)-hydroxymethyl-4-(R)-tert.-betylsulfonyl-2-azetidinone.

6. The process according according to claim 3 wherein R₁ is methyl and the configuration about the carbon atom to which R₁ is bound is R, Y is tert.-butylsufonyl, and R₄' is 1-methoxybenzyl, said (3S)-3,4-trans-disubstituted azetidinone thereby yielded being 1-p-methoxybenzyl-3-(S)-(1? -(R)-hydroxyethyl)-4-(R)-tert.-butylsulfonyl-2-azetidinone.

7. The process according to claim 1 wherein said aprotic solvent is tetrahydrofuran and said treatment is conducted at temperatures of from about −50° C. to about 50° C.

8. The process according to claim 4 wherein said source of fluoride ion is a salt of hydrogen fluoride and an organic base.

9. The process according to claim 6 wherein said salt is tetra(n-butyl)ammonium fluoride.

10. The process according to claim 1 including the step of treating said (3S)-3,4-trans-disubstituted azetidinone with an oxidizing agent capable of removing R₄' and producing a 1-unsubstituted azetidinone of the formula:

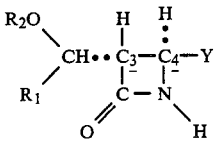

in which R₁, R₂, and Y and the configuration are as therein defined.

11. The process according to claim 10 wherein R₁ is hydrogen or methyl, Y is —SO₂R₃ or —COOR₃, R₃ is tert.-lower alkyl or phenyl, and R₄' in said (3S)-3,4-trans-disubstituted azetidinone azetidinone is benzyl or phenyl each of which is substituted with one or two methoxy groups.

12. The process according to claim 11 wherein R₃ is tert.-butyl or phenyl and R₄' in said (3S)-3,4-trans-disubstituted azetidinone is 4-methoxybenzyl, 2,4-dimethoxybenzyl, 4-methoxyphenyl, or 3,4-dimethoxyphenyl.

13. The process according to claim 10 wherein R₁ is hydrogen and Y is tert.-butylsulfonyl, said 1-unsubstituted azitidinone thereby yielded being 3-(S)-hydroxymethyl-4-(R)-tert.-butylsulfonyl-2-azetidinone.

14. The process according to claim 10 wherein R₂ is methyl, and the configuration about the carbon atom to which R₂ is bound is R, and Y is tert.butylsolfonyl, said 1-unsubstituted azetidinone thereby yielded being 3-(S)-(1'-(R)-hydroxyethyl)-4-(R)-tert.-butylsulfonyl-2-azetidinone.

15. The process according to claim 10 wherein said oxidizing agent is sodium or potassium peroxodisulfate or is a cerium (IV) salt.

16. The process according to claim 10 wherein R₂ is said hydroxy protecting group.

17. The process according to claim 16 wherein R₂ is 2,2,2-trichloroethoxycarbonyl, allyloxycarbonyl, benzyloxycarbonyl, p-nitrobenzyloxycarbonyl, trimethylsilyl or dimethyl-tert.-butylsilyl.

18. The process according to claim 16 wherein a (3S)-3,4-trans-disubstituted azetidinone in which $R_2$ is hydrogen is converted to the corresponding (3S)-3,4-trans-disubstituted azetidinone in which $R_2$ is said hydroxy protecting group prior to said oxidation and said $R_2$ is removed following said oxidation to produce said 1-unsubstituted azetidinone in which $R_2$ is hydrogen.

19. The process according to claim 18 wherein $R_2$ is 2,2,2-trichloroethoxycarbonyl, allyloxycarbonyl, benzyloxycarbonyl, p-nitrobenzyloxycarbonyl, trimethylsilyl or dimethyl-tert.-betylsilyl.

* * * * *